US011185235B2

(12) United States Patent
Watanabe et al.

(10) Patent No.: US 11,185,235 B2
(45) Date of Patent: Nov. 30, 2021

(54) INFORMATION PROCESSING METHOD, INFORMATION PROCESSING DEVICE, AND RECORDING MEDIUM

(71) Applicant: Panasonic Intellectual Property Management Co., Ltd., Osaka (JP)

(72) Inventors: Kazuhiro Watanabe, Osaka (JP); Tomohiko Kitamura, Osaka (JP); Yasuo Kohashi, Osaka (JP); Masaru Yamaoka, Osaka (JP); Toshiaki Tanaka, Hyogo (JP); Kenji Masuda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 523 days.

(21) Appl. No.: 15/915,008

(22) Filed: Mar. 7, 2018

(65) Prior Publication Data

US 2018/0271379 A1    Sep. 27, 2018

(30) Foreign Application Priority Data

Mar. 27, 2017   (JP) .............................. JP2017-061295
Nov. 22, 2017   (JP) .............................. JP2017-224454

(51) Int. Cl.
*A61B 5/01*   (2006.01)
*G06N 20/00*   (2019.01)
(Continued)

(52) U.S. Cl.
CPC .............. *A61B 5/01* (2013.01); *A61B 5/7264* (2013.01); *A61B 5/746* (2013.01); *G06F 16/285* (2019.01);
(Continued)

(58) Field of Classification Search
CPC .......... F24F 2120/00–20; A61B 5/7264–7267; A61B 5/01–015; A61B 5/11;
(Continued)

(56) References Cited

U.S. PATENT DOCUMENTS 5,059,796 A * 10/1991 Nakamura ........... G08B 13/194
                                                     250/330
5,187,943 A *  2/1993 Taniguchi .......... B60H 1/00742
                                                      62/180
(Continued)

FOREIGN PATENT DOCUMENTS

CN       104471362 A      3/2015
CN       106461254 A      2/2017
(Continued)

OTHER PUBLICATIONS

Manubhai ["Occupant Posture Analysis With Stereo and Thermal Infrared Video: Algorithms and Experimental Evaluation" IEEE Transactions On Vehicular Technology, vol. 53, No. 6, Nov. 2004] (Year: 2004).*

(Continued)

*Primary Examiner* — Oommen Jacob
(74) *Attorney, Agent, or Firm* — Greenblum & Bernstein, P.L.C.

(57) ABSTRACT

An information processing device obtains measurement data for calculating biological information of a measurement subject from a sensor that performs measurement without contact. Based on content of the measurement data, the measurement data is classified into a group associated with at least a position of the measurement subject, the biological information is calculated from the classified measurement data, and the calculated biological information is compared (Continued)

with a reference value associated with a group to which the measurement data belongs. Then, a notification is made based on the comparing.

10 Claims, 20 Drawing Sheets

(51) Int. Cl.
  *G06F 16/28* (2019.01)
  *A61B 5/00* (2006.01)
  *G06N 3/08* (2006.01)
  *A61B 5/11* (2006.01)
(52) U.S. Cl.
  CPC ............... *G06N 3/08* (2013.01); *G06N 20/00* (2019.01); *A61B 5/0077* (2013.01); *A61B 5/1116* (2013.01); *A61B 2503/08* (2013.01); *A61B 2505/07* (2013.01)
(58) Field of Classification Search
  CPC ..... A61B 5/1116; A61B 5/746; A61B 5/0077; A61B 2503/08; A61B 2505/07; G06N 3/08; G06N 20/00; G06F 16/285
  See application file for complete search history.

(56) References Cited

U.S. PATENT DOCUMENTS

| | | | | |
|---|---|---|---|---|
| 5,384,716 A * | 1/1995 | Araki | ............... | G05D 23/1917 702/134 |
| 6,407,389 B1 * | 6/2002 | Nishii | ............... | B60R 25/1004 250/338.1 |
| 6,522,266 B1 * | 2/2003 | Soehren | ............... | A61B 5/7264 340/988 |
| 6,550,686 B2 * | 4/2003 | Kawai | ............... | B60H 1/00792 236/49.3 |
| 7,027,621 B1 * | 4/2006 | Prokoski | ............ | G06K 9/00248 180/272 |
| 7,661,706 B2 * | 2/2010 | Yoshifuku | ......... | B60R 21/01538 280/735 |
| 10,292,625 B2 * | 5/2019 | Shinar | ............... | A61B 5/6892 |
| 10,503,987 B2 * | 12/2019 | Banno | ............... | A61B 5/1103 |
| 10,794,610 B2 * | 10/2020 | Nakamura | ............ | F24F 11/89 |
| 2003/0058339 A1 * | 3/2003 | Trajkovic | ............ | G06K 9/00335 348/155 |
| 2003/0059081 A1 * | 3/2003 | Trajkovic | ............ | G08B 13/19613 382/100 |
| 2003/0107707 A1 * | 6/2003 | Fisher | ............... | G02C 7/027 351/159.74 |
| 2005/0103876 A1 * | 5/2005 | Martinez | ............ | B60H 1/00742 236/94 |
| 2006/0208169 A1 * | 9/2006 | Breed | ............... | G06K 9/00624 250/221 |
| 2007/0274572 A1 * | 11/2007 | Nishino | ............... | A61B 5/6825 382/118 |
| 2008/0243027 A1 * | 10/2008 | Nakayama | ............... | A61B 5/01 600/549 |
| 2009/0030576 A1 * | 1/2009 | Periot | ............... | B60R 21/01508 701/45 |
| 2009/0210193 A1 * | 8/2009 | Nagase | ............... | F24F 11/30 702/152 |
| 2010/0063636 A1 * | 3/2010 | Matsumoto | ............... | F24F 11/30 700/276 |
| 2010/0086214 A1 * | 4/2010 | Liang | ............... | G06K 9/00248 382/197 |
| 2011/0285982 A1 * | 11/2011 | Breed | ............... | B60N 2/0232 356/4.01 |
| 2012/0310417 A1 * | 12/2012 | Enohara | ............ | G06K 9/00771 700/276 |
| 2013/0255909 A1 * | 10/2013 | Matsumoto | ......... | B60H 1/00814 165/11.1 |
| 2014/0020860 A1 * | 1/2014 | Matsumoto | ............... | F24F 11/30 165/11.1 |
| 2015/0204556 A1 * | 7/2015 | Kusukame | ............... | F24F 11/30 165/237 |
| 2016/0363340 A1 * | 12/2016 | Shikii | ............... | F24F 11/62 |
| 2017/0051937 A1 | 2/2017 | Toyoshima et al. | | |
| 2018/0061044 A1 * | 3/2018 | Woodbridge | ......... | G06T 7/0016 |
| 2018/0271379 A1 * | 9/2018 | Watanabe | ............... | G06N 20/00 |

FOREIGN PATENT DOCUMENTS

| | | |
|---|---|---|
| JP | 2009-119896 | 6/2009 |
| JP | 2015-055393 | 3/2015 |

OTHER PUBLICATIONS

Chinese Search Report (English Language Translation), dated Dec. 3, 2020, for the related Chinese Patent Application No. 201810228173.7.

* cited by examiner

INFORMATION PROCESSING METHOD, INFORMATION PROCESSING DEVICE, AND RECORDING MEDIUM

BACKGROUND

1. Technical Field

The present disclosure relates to a technique for grasping a biological state of a measurement subject.

2. Description of the Related Art

In recent years, techniques for sensing biological information of a measurement subject without contact are being developed. For example, in Japanese Unexamined Patent Application Publication No. 2009-119896, there is disclosed an air conditioner whose objective is to performs air conditioning in such a way that a person staying in a room feels comfortable. The air conditioner obtains a captured image of a room and a temperature distribution image in the room, calculates a face position based on the captured image, obtains, from the temperature distribution image, temperature information at a location separated from the face position by a predetermined distance, and performs air conditioning according to the obtained temperature information.

In Japanese Unexamined Patent Application Publication No. 2015-55393, there is disclosed the following technique, and an objective thereof is to stably calculate the temperature of a crew's face by considering the direction of the crew's face. That is, Japanese Unexamined Patent Application Publication No. 2015-55393 discloses a technique in which a face region of a crew is extracted from a temperature distribution map obtained by an infrared (IR) camera, contribution ratios of a center region of the face region and surrounding regions positioned at right and left sides of the center region are adjusted so that the area of the center region and the area of the surrounding region become equal, and a face temperature of the crew is calculated based on the adjusted contribution ratios.

SUMMARY

However, in related art, there are cases where the biological state of a measurement subject is difficult to grasp correctly. The state of blood flow in the body differs from person to person, and it is known that, for example, in a human body with one-sided paralysis, the body temperature on paralysis side is substantially low. Accordingly, it is difficult to correctly grasp a change in body temperature of a human body only by measuring the body temperature of a face part while adjusting the contribution ratios of the center region and the surrounding regions so that the area of the center region and the area of the surrounding region become equal, as disclosed in Japanese Unexamined Patent Application Publication No. 2015-55393.

The invention disclosed in Japanese Unexamined Patent Application Publication No. 2009-119896 detects the temperature at a location separated from the face position by a predetermined distance. Thus, it is difficult to correctly grasp the body temperature of a human body itself.

One non-limiting and exemplary embodiment provides a technique for correctly grasping a biological state of a measurement subject.

In one general aspect, the techniques disclosed here features an information processing method comprising: obtaining measurement data for calculating biological information of a measurement subject from a sensor that performs measurement without contact; based on content of the measurement data, classifying the measurement data into a group associated with at least a position of the measurement subject, calculating the biological information from classified measurement data, and comparing calculated biological information with a reference value associated with a group to which the measurement data belongs; and making a notification based on the comparing.

An embodiment of the present disclosure enables correct grasping of a biological state of a measurement subject.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
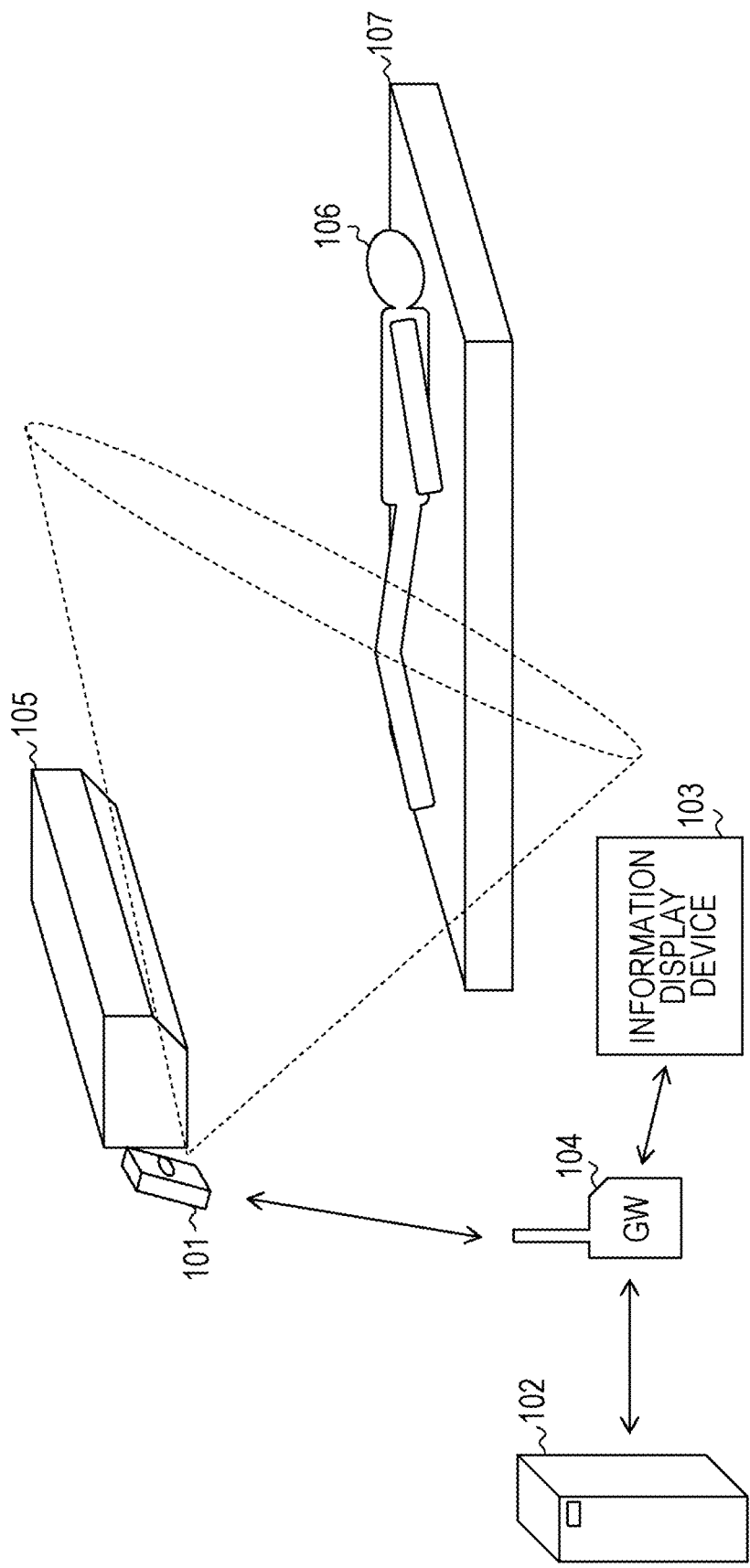
FIG. 1 is a diagram illustrating an overview of a biological information sensing device to which an information processing device according to Embodiment 1 is applied.

Underlying Knowledge Forming Basis of Present Disclosure

In elder care, it is said that keeping records of changes in living conditions and the body temperature is highly desirable for managing daily health of an elderly person. There is a plan for a health management system that periodically measures biological information of a human body such as a body temperature and the like, compares the measured value with a reference value, and makes a notification if a change such as an abnormal feature and the like is detected.

In related art, as means for measuring a body temperature of a human body, a thermometer and a radiant heat sensor are known. These means grasp the body temperature by making measurement at specific part of a human body such as armpit, inner ear, front part of face, and the like.

However, in cases where such contact-type means are used in the health management system, it is necessary to bring a thermometer into contact with armpit part to measure the body temperature or to use a special device such as an inner-ear thermometer and the like for bringing into contact with a human body to measure the body temperature. Therefore, it is necessary to ask a measurement subject to be still or to measure the body temperature of a measurement subject while being attended by a measurement operator. As a result, there is an issue of placing burden on both the measurement operator and the measurement subject.

It is conceivable to apply, to the system performing health management, the method of Japanese Unexamined Patent Application Publication No. 2015-55393 where the body temperature measurement is performed using a thermal image sensor that measures the body temperature without contact. Here, in Japanese Unexamined Patent Application Publication No. 2015-55393, a single body temperature is calculated in the end by adjusting the contribution ratios of respective regions. Thus, a health management system to which the method of Japanese Unexamined Patent Application Publication No. 2015-55393 is applied only needs to prepare a single reference body temperature for detecting presence or absence of a change.

However, in a human body with one-sided paralysis, the body temperature on paralysis side greatly differs from the body temperature of non-paralysis side. Therefore, in a case where a single reference body temperature is used to detect presence or absence of a change in body temperature, when the body temperature on the paralysis side is measured because of the position of a measurement subject at the time of measurement, it is possible to erroneously determine that, for example, the body temperature is normal because a measured body temperature is lower than the reference body temperature even though the measurement subject actually has fever. On the other hand, when the body temperature on the non-paralysis side is measured because of the position of a measurement subject at the time of measurement, it is possible to erroneously determine that, for example, the measurement subject has fever because the measured body temperature is higher than the reference body temperature even though the measurement subject actually has a normal body temperature.

The present disclosure is made to resolve such issues and to provide a technique that enables correct grasping of a biological state of a measurement subject without placing burden on both the measurement subject and a measurement operator.

An information processing method according to one aspect of the present disclosure includes:
  obtaining measurement data for calculating biological information of a measurement subject from a sensor that performs measurement without contact;
  based on content of the measurement data, classifying the measurement data into a group associated with at least a position of the measurement subject, calculating the biological information from classified measurement data, and comparing calculated biological information with a reference value associated with a group to which the measurement data belongs; and
  making a notification based on the comparing.

According to the present aspect, the measurement data measured by the sensor are classified into the groups based on the positions of a measurement subject, the reference value associated with the classified group is compared with the classified measurement data, and a notification is made based on the comparing. Accordingly, a notification can be made upon correctly grasping the biological state of a measurement subject regardless of the position of the measurement subject at the time of measurement. In other words, the occurrence of processing on an erroneous notification can be reduced. Accordingly, processing load regarding the notification can be reduced. Further, according to the present aspect, the biological information is measured without contact. This enables grasping of the biological state without placing burden on both the measurement subject and the measurement operator.

In the foregoing aspect, in the classifying of the measurement data, the measurement data may be classified into the group using a machine learning model, the machine learning model being a model having machine-learned about classification of the measurement data into the group based on content of the measurement data, and the reference value may be a representative value of the biological information in the group and is calculated from the measurement data classified into the group. In this way, the machine learning model can classify measurement data, thereby enabling more appropriate classification than a rule-based classification. Further, the reference value is determined from the measurement data actually classified. This enables the use of a more accurate reference value in the foregoing process for comparing.

In the foregoing aspect, the information processing method may further include:

causing the machine learning model to perform machine learning about classification of the measurement data into the group based on content of the measurement data, wherein in the machine learning, the representative value of the biological information in the group may be calculated from measurement data classified into the group as the reference value of the group.

According to the present aspect, the representative value of the biological information of each group is calculated by the machine learning from the measurement data classified into each group, and this representative value is calculated as the reference value. This enables calculation of the reference value for each group suited for a measurement subject.

In the foregoing aspect, the sensor may be a thermal image sensor, the biological information may be a body temperature,
the measurement data may be thermal image data obtained by the thermal image sensor,
in the classifying the measurement data, the thermal image data may be classified into the group based on a characteristic of a region indicating the measurement subject, the region being included in the thermal image data obtained by the thermal image sensor, and
in the comparing, the body temperature of the measurement subject may be calculated from classified thermal image data, and a calculated body temperature may be compared with a reference value associated with a group to which the classified thermal image data belongs.

According to the present aspect, the sensor is constituted by the thermal image sensor, thereby enabling correct grasping of the biological state of a measurement subject.

In the foregoing aspect, the sensor may be a radio wave sensor, the biological information may be an activity amount including at least one of a body motion value, a breathing rate, and a heart rate of the measurement subject,
the measurement data may be activity amount data indicating the activity amount obtained by the radio wave sensor,
in the classifying the measurement data, the activity amount data may be classified into the group based on waveform information of the activity amount data obtained by the radio wave sensor, and
in the comparing, the activity amount of the measurement subject may be calculated from classified activity amount data, and a calculated activity amount may be compared with a reference value associated with a group to which the classified activity amount data belongs.

According to the present aspect, the sensor is constituted by the radio wave sensor, thereby enabling more accurate detection of at least one of the body motion value, the breathing rate, and the heart rate of the measurement subject.

In the foregoing aspect, in a case where the number of pieces of the measurement data not corresponding to any one of the groups exceeds a reference number, information prompting re-learning of the machine learning model may be generated.

According to the present aspect, the information prompting re-learning of the machine learning is generated in the case where the number of pieces of the measurement data not corresponding to any one of the groups exceeds a reference number during execution of a process for comparing measurement data and a reference value. Accordingly, for example, a manager who becomes aware of this information can re-execute the machine learning. In this way, even in the case where the measurement subject takes a position that has not been observed at the time of the machine learning during the execution of a process for comparing measurement data and a reference value.

In the foregoing aspect, the information processing method may further include obtaining time data indicating time of measurement of the measurement data, wherein
in the comparing, whether or not the measurement data is measured at a predetermined time of day may be determined based on the time data, and the comparing may be performed when determined that the measurement data is measured at the predetermined time of day.

According to the present aspect, a process for comparing is executed when measurement data belongs to the predetermined time of day. Accordingly, for example, the process for comparing can be performed using measurement data measured at time of day in which the state of a measurement subject is stable, thereby enabling more correct grasping of the biological information.

In the foregoing aspect, the position may be a direction of body of the measurement subject. In this way, measurement data can be classified into a group associated with the direction of body of the measurement subject. Characteristics of a human body such as the blood flow and the like change depending on the direction of body. That is, the reference value of the biological information such as the body temperature and the like changes depending on the direction of body. Accordingly, by using an appropriate reference value, it is possible to determine whether or not there is abnormality in the measurement subject.

In the foregoing aspect, the notification based on the comparing may be a comparison result between the biological information and the reference value or abnormality of the measurement subject. This enables a person who can receive a notification to be aware of abnormality of a measurement subject.

The forgoing aspect can be achieved as a method of making constituting processing means to steps. Further, the present disclosure can be achieved as a program that causes a computer to execute steps included in the method. Further, the present disclosure can be achieved as a computer-readable recording medium, such as CD-ROM or the like, storing the program thereon.

Embodiment 1

FIG. 1 is a diagram illustrating an overview of a biological information sensing device to which an information processing device according to Embodiment 1 is applied. In FIG. 1, the sensing device 101 includes a thermal image sensor and placed in a room such as a bedroom and the like, where a bed 107 is placed. The sensing device 101 is, for example, placed alongside an air conditioner 105. Preferably, for example, the sensing device 101 is placed in an inconspicuous place such as in the vicinity of a side of the air conditioner 105. For example, the sensing device 101 is installed in a room in such a way that a measurement range of the sensing device 101 covers the entire area of the bed 107.

The sensing device 101 obtains thermal image data indicating a thermal distribution in a room in which a human body 106 (one example of the measurement subject) is included. The sensing device 101 transmits the obtained thermal image data to an information processing device 102 via a gateway (hereinafter, referred to as GW) 104. The information processing device 102 classifies the thermal image data into respective groups based on the position of the human body 106 and manages the classified thermal image data. The GW 104 may be referred to as a router.

Here, the room may be, for example, a room in a senior nursing home, where the human body 106 being a caring target stays, or a room in a house where the human body 106 lives.

Upon detection of a change in body temperature of the human body 106 by comparing the thermal image data classified into respective groups and the thermal image data measured in this time, the information processing device 102 transmits alerting information indicating abnormal body temperature of the human body 106 to the information display device 103 via the GW 104. Upon receipt of the alerting information, the information display device 103 issues an alert. This enables a manager of the human body 106 to aware abnormal body temperature of the human body 106.

With regard to the manager of the human body 106, for example, a caregiver who takes care of the human body 106 or a manager of a nursing home may play such role.

Figure 2:
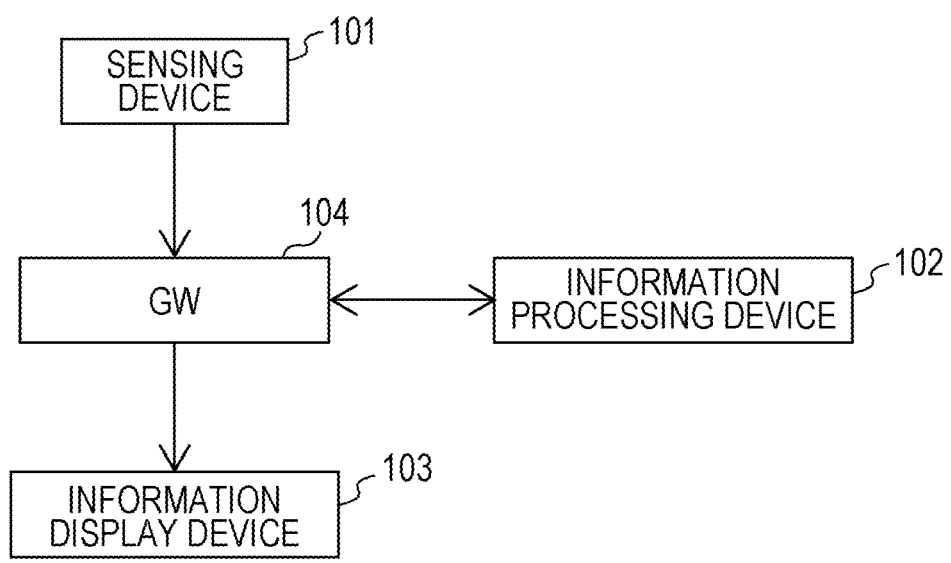
FIG. 2 is a diagram illustrating one example of connection configuration of the biological information sensing device.

FIG. 2 is a diagram illustrating one example of a connection configuration of the biological information sensing device. As illustrated in FIG. 2, the biological information sensing device includes the sensing device 101, the information processing device 102, the information display device 103, and the GW 104. The sensing device 101, the information processing device 102, and the information display device 103 are each connected to the GW 104 via their respective predetermined networks. As the predetermined network, for example, a wired LAN, a wireless LAN, or a LAN that is a combination thereof may be employed.

Figure 3:
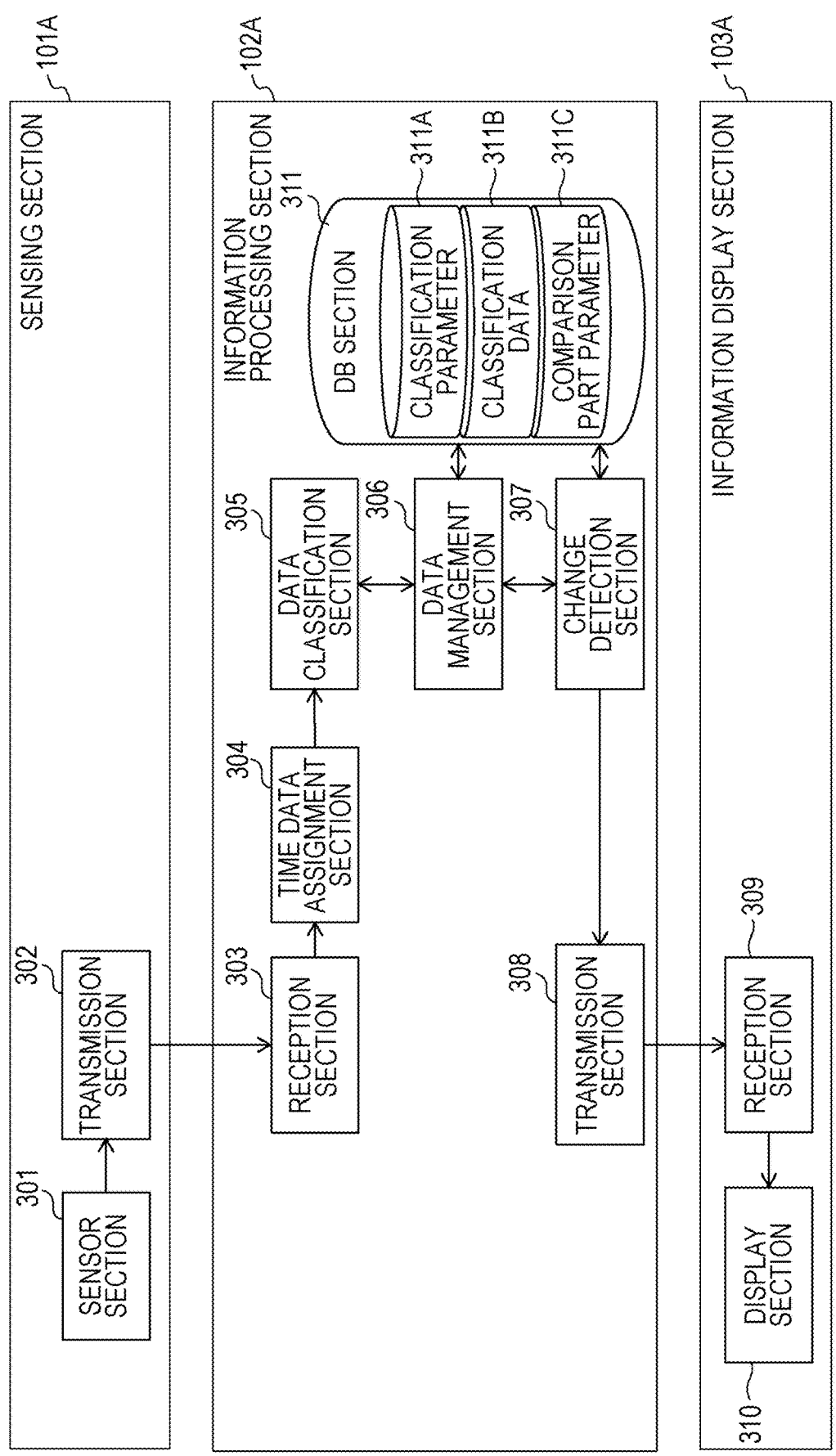
FIG. 3 is a diagram illustrating a configuration of functions of a biological information sensing device to which an information processing device according to Embodiment 1 is applied.

FIG. 3 is a diagram illustrating a configuration of functions of the biological information sensing device to which an information processing device according to Embodiment 1 is applied. The biological information sensing device includes a sensing section 101A corresponding to the sensing device 101, an information processing section 102A corresponding to the information processing device 102, and an information display section 103A corresponding to the information display device 103.

The sensing section 101A (one example of the sensor) includes a sensor section 301 and a transmission section 302, and measures biological information without contact. The sensor section 301 is constituted by, for example, a thermal image sensor and obtains thermal image data (one example of the measurement data) by capturing an image of the room of the human body 106 at predetermined sampling intervals. The transmission section 302 is constituted by, for example, a communication circuit of a wireless LAN or a wired LAN and transmits the thermal image data obtained by the sensor section 301 at the predetermined sampling intervals to the information processing section 102A.

The information processing section 102A includes a reception section 303, a time data assignment section 304, a data classification section 305, a data management section 306, a change detection section 307, a transmission section 308, and a DB section 311.

The reception section 303 (one example of the acquisition section) is constituted by, for example, a communication circuit of a wireless LAN or a wired LAN and receives the thermal image data transmitted from the sensing section 101A at predetermined sampling intervals.

The time data assignment section 304 assigns a measurement time to the thermal image data received at the reception section 303. Here, as the measurement time, for example, time of obtainment of the thermal image data by the reception section 303 is assigned. The measurement time is composed of, for example, data indicating year/month/day/hour/minute/second.

The data classification section 305 obtains a plurality of the thermal image data by sequentially obtaining thermal image data to which time data is assigned by the time data assignment section 304 during a learning phase where learning is performed on groups based on the position. Further, the data classification section 305 learns about the groups by classifying the thermal image data based on characteristics of the region indicating the human body 106 included in each of the plurality of pieces of obtained thermal image data. As a characteristic of pixel, a contour of a region indicating the human body 106 or a temperature distribution forming this region is employed.

Here, the data classification section 305, for example, learns about the groups by machine learning. Here, as the machine learning, for example, supervised machine learning or unsupervised machine learning using a neural network may be employed. In the case of supervised machine learning, the data classification section 305 may learn, for example, weight coefficients of a neural network so as to output a group identifier that identifies a group base on the position given to each thermal image data in advance.

Here, as the position given in advance, for example, the direction of the human body 106 may be employed. As the direction of the human body 106, for example, at least following four patterns may be employed: "front" indicating the direction of the human body 106 when viewed from the front side; "left" indicating the direction of the human body 106 when viewed from the left side using the front side as reference; "right" indicating the direction of the human body 106 when viewed from the right side using the front side as reference; and "back" indicating the direction of the human body 106 when viewed from the back side. Further, as the direction of the human body 106, for example, a depth pattern may be added to each of the four patterns of front, back, left, and right. As the depth pattern, for example, a pattern corresponding to an incremental distance to the thermal image sensor may be employed. In this case, as the depth pattern, for example, "close", "normal", "far", and the like may be employed. In the case where there are four patterns of front, back, left, and right for the direction of the human body 106 and there are three patterns of "close", "normal", and "far" for the depth of the human body 106, thermal image data is classified into twelve groups, which is equal to four times three, depending on the position and the depth. Here, the reason to include the depth in the consideration is to consider a decrease in measurement accuracy of the thermal image sensor proportional to the distance from the thermal image sensor to the human body 106. Alternatively, as the direction of the human body 106, a direction other than the foregoing four patterns (for example, diagonally forward right, diagonally forward left, diagonally backward right, diagonally backward left) may be added, or one or more of the foregoing four patterns may be omitted.

In the case where unsupervised machine learning is employed, the data classification section 305 may employ a deep neural network whose number of stages is greater than that of a typical neural network. In the case where the deep neural network is employed, even without setting the position and the depth in advance, the data classification section 305 can learn about the groups by classifying thermal image data according to characteristics of the region indicating the human body 106 included in the thermal image data.

Alternatively, the data classification section 305 may learn about the groups using a method other than machine learning. In the case where a method other than machine learning is employed, the data classification section 305 first extracts a region of the human body 106 from thermal image data. In this case, for example, the data classification section 305 may extract a region of the human body 106 by calculating a Histograms of Oriented Gradients (HOG) feature value from thermal image data and dividing the thermal image data into the region of the human body 106 and the background region based on the HOG feature value. Next, the data classification section 305 may determine the direction of the human body 106 by using the contour of the extracted region of the human body 106 and a spatial relationship between the nose and the mouth on a face part. Here, the face part can be extracted from the shape of the human body 106, and the locations of the nose and the mouth can be acquired from the thermal distribution of the face part. Further, in this case, as the direction of the human body 106 to be determined, directions determined in advance such as the directions of the foregoing four patterns of front, back, left, and right may be employed.

Next, the data classification section 305 classifies thermal image data by assigning a group identifier associated with the determined direction to the thermal image data. In this case, the data classification section 305 may further classify thermal image data into the foregoing respective depth patterns based on the size of the face part. In this case, the data classification section 305 may classify thermal image data by assigning a group identifier, which is determined for each combination of the direction and the depth of the human body 106, to the thermal image data.

On the other hand, in a detection phase where a change in biological information is detected, the data classification section 305 sequentially obtains the thermal image data to which time data is assigned by the time data assignment section 304. Further, the data classification section 305 classifies the obtained thermal image data into one of the groups that are learned in the learning phase based on the characteristics of the region indicating the human body 106 included in each of the obtained thermal image data. For example, in the case where a neural network is employed in the learning phase, the data classification section 305 may input thermal image data being a detection target to the neural network in the detection phase, and determine the group to which the thermal image data belongs.

Further, in the case where a method other than the foregoing machine learning is employed in the learning phase, the data classification section 305 may use such method to determine the group to which the detection-target thermal image data belongs.

In the learning phase, the data management section 306 calculates, as a reference value of each group, a representative value of the body temperature for each of the groups from the thermal image data classified in the data classification section 305. Here, it is assumed that the reference value corresponds to a normal body temperature of the human body 106, and an average temperature of the human body for each group is employed as the reference value, the average temperature being obtained from the thermal image data classified to the group.

Further, the data management section 306 manages the reference values by storing the calculated reference values of the respective groups in the DB section 311. The data management section 306 may update the reference value based on a classification result of thermal image data even in the detection phase.

The change detection section 307 (one example of the comparison section) detects presence or absence of a change in body temperature of the human body 106 by, in the detection phase, calculating a body temperature (one example of the biological information) of the human body 106 from thermal image data classified to one of the groups by the data classification section 305 and comparing the calculated body temperature with the reference value associated with the group to which the thermal image data belongs. Further, when a change in body temperature is detected, the change detection section 307 generates alerting information indicating abnormal body temperature. Here, it is assumed that the reference value corresponds to a normal body temperature of the human body 106. Thus, for example, the change detection section 307 may determine that there is a change in body temperature if a temperature difference between the body temperature calculated from target thermal image data and the normal body temperature indicated as the reference value is equal to or larger than plus or minus one degree Celsius. Here, it is determined that there is a change in body temperature if there is the temperature difference equal to or larger than plus or minus one degree Celsius. However, the present disclosure is not limited thereto and may alternatively determine that there is a change in body temperature if there is the temperature difference equal to or larger than a predetermined temperature other than the one degree Celsius (for example, 0.5 degrees Celsius, 1.5 degrees Celsius, and the like).

Here, the change detection section 307 may detect part (for example, face part) designated by a comparison part parameter 311C, which will be described below, from thermal image data, and calculate, for example, an average temperature of the body temperature of the human body 106 at the detected part.

The transmission section 308 is constituted by, for example, a communication circuit of a wireless LAN or a wired LAN and transmits alerting information to the information display section 103A when the change detection section 307 generates the alerting information.

The database (hereinafter, referred to as DB) section 311 is constituted by, for example, a non-volatile storage device and stores therein various data that the data management section 306 manages. The DB section 311 stores therein classification parameters 311A, classification data 311B, and comparison part parameters 311C.

The classification parameters 311A are, for example, weight coefficients of a neural network obtained as a result of learning in the case where the neural network is employed as the learning phase.

The classification data 311B is thermal image data classified into the respective groups by the data classification section 305 in the learning phase and the detection phase.

The comparison part parameter 311C is a parameter indicating part of the human body 106, which is used as a comparison target at the time of detection by the change detection section 307. For example, as the comparison part parameter, information designating a face is employed when the face is used as the comparison target.

In the case where supervised machine learning is employed, the DB section 311 may store therein information indicating the position and the depth that serves as a classification target determined in advance.

The information display section 103A is constituted by, for example, a computer available for the manager of the human body 106, further includes a reception section 309 and a display section 310, and outputs alerting information. Alternatively, the information display section 103A may be constituted by a desktop computer or by a tablet terminal or a portable computer such as a smartphone and the like.

The reception section 309 is constituted by a communication circuit of a wireless LAN or a wired LAN and receives alerting information transmitted from the information processing section 102A. The display section 310 is constituted by, for example, a liquid crystal display or an organic EL display, and displays the alerting information. In this case, the display section 310 may display, for example, a message or the like indicating that the body temperature of the human body 106 is not normal. Alternatively, the information display section 103A may output, from a loudspeaker not illustrated in the figure, a sound message indicating that the body temperature of the human body 106 is not normal.

Figure 4:
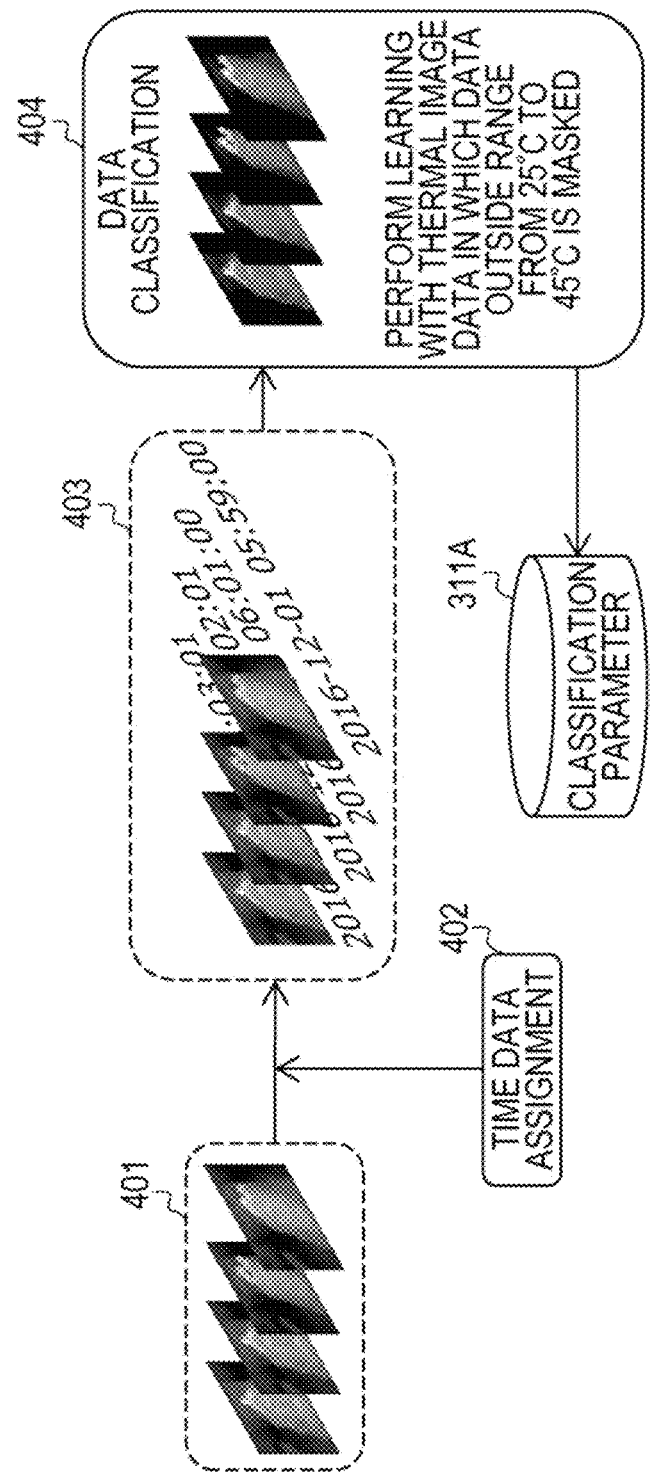
FIG. 4 is a diagram illustrating a data processing method in a learning phase.
Figure 5:
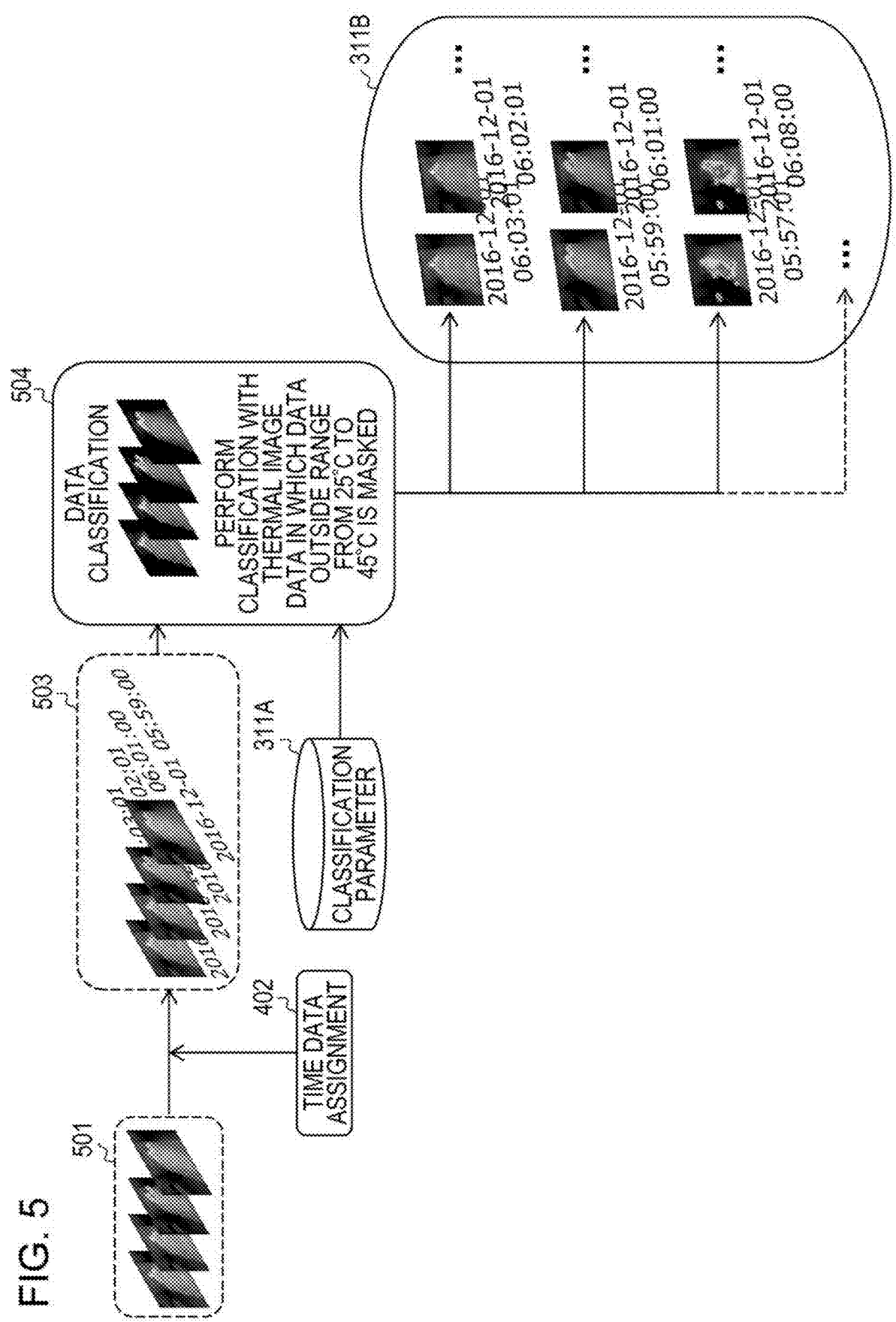
FIG. 5 is a diagram illustrating a data processing method in a detection phase.
Figure 6:
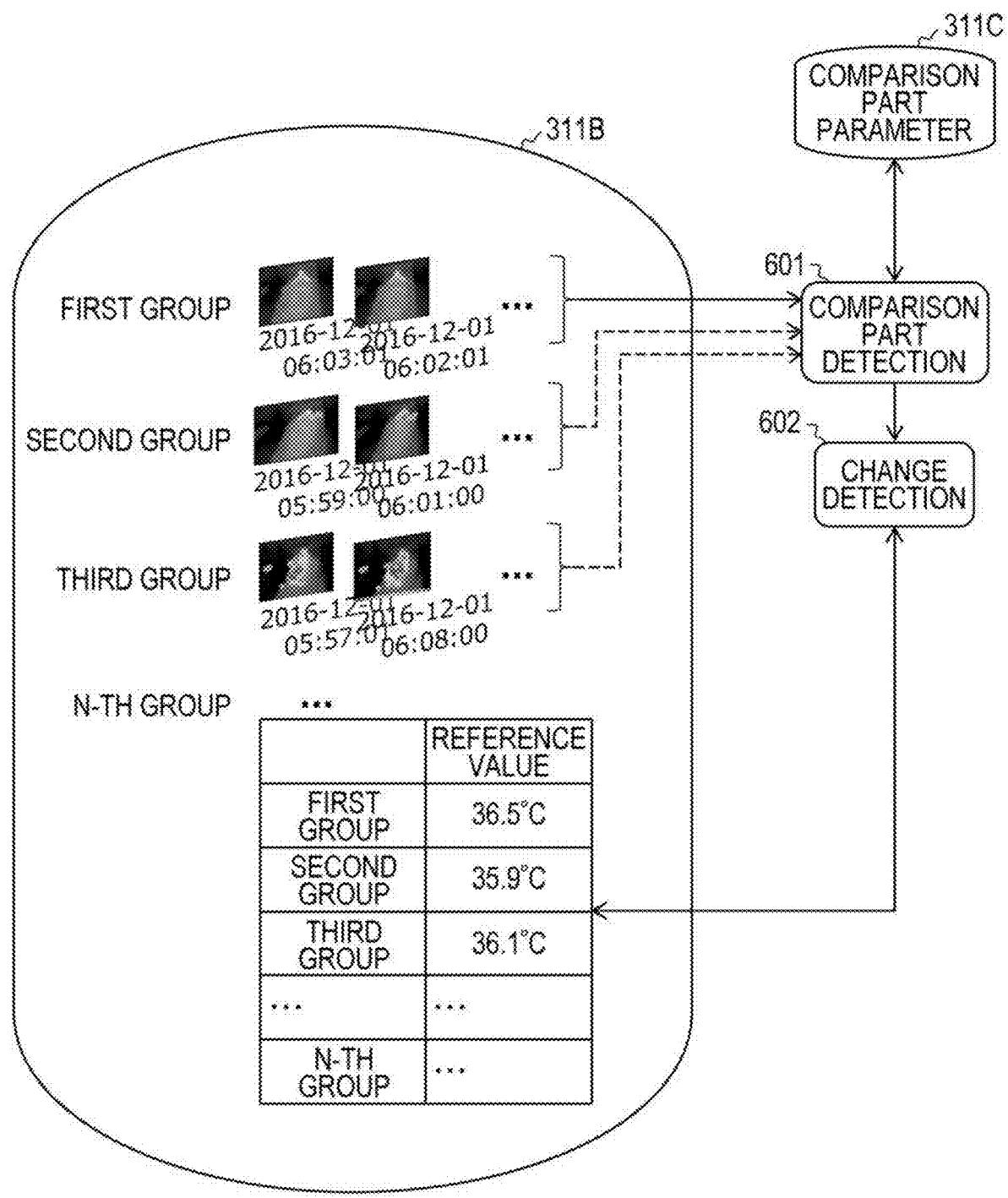
FIG. 6 is a diagram that follows FIG. 5 and illustrates the data processing method in the detection phase.

Next, a data processing method in the information processing section 102A is described with reference to FIG. 4 to FIG. 6. FIG. 4 is a diagram illustrating a data processing method in the learning phase. FIG. 5 is a diagram illustrating a data processing method in the detection phase. FIG. 6 is a diagram that follows FIG. 5 and illustrates the data processing method in the detection phase.

Referring to FIG. 4, when the biological information sensing device is installed in a site, the information processing section 102A generates the classification parameters 311A by learning thermal image data for a certain period of time. First, the time data assignment section 304 assigns time data (402) to each of thermal image data (401) obtained by the sensing section 101A. Next, the data classification section 305 performs, for each of the thermal image data (403) to which time data is assigned, a mask process to mask the region whose temperature range is other than a predetermined temperature range (for example, 25 degrees Celsius to 45 degrees Celsius). Next, by performing machine learning using a neural network, the data classification section 305 classifies thermal image data into each group of the human body 106 and generates the classification parameters 311A (404). Here, as the predetermined temperature range, the range from 25 degrees Celsius to 45 degrees Celsius is employed. However, for example, by employing the range from 30 degrees Celsius to 45 degrees Celsius or the like, the difference between the human body 106 and an object (for example, furniture or the like) other than the human body 106 may be made clearer. It is assumed that the predetermined temperature range corresponds to a temperature range that the human body 106 can have.

Next, referring to FIG. 5, when the learning phase ends, the detection phase starts. First, as in the learning phase, the time data assignment section 304 assigns time data (402) to thermal image data (501) obtained by the sensing section 101A. Next, as in the learning phase, the data classification section 305 performs a mask process on the thermal image data (503), to which time data is assigned, to mask the region whose temperature range is other than a predetermined temperature range. Next, by inputting, to the neural network generated in the learning phase, the thermal image data in which the region whose temperature range is other than the predetermined temperature range is masked, the data classification section 305 classifies the thermal image data into one of the groups having been classified in the learning phase (504). Here, as the groups, there are the first to the Nth groups. Thus, the thermal image data is classified to one of the first to Nth groups (N is an integer equal to or larger than one). In this way, the detection-target thermal image data is classified according to characteristics of a region indicating the human body 106. The classified thermal image data is stored in the DB section 311 as the classification data 311B. Note that the neural network generated by the learning phase is one example of a machine learning model.

Next, referring to FIG. 6, the change detection section 307 reads thermal image data being a detection target from the classification data 311B, and detects part designated by the comparison part parameter 311C from the read thermal image data (601). For example, if the comparison part parameter 311C designates a face part, the change detection section 307 detects a face part from thermal image data being a detection target.

Next, the change detection section 307 detects presence or absence of a change in body temperature of the human body 106 (602) by calculating a body temperature of the part detected from the thermal image data and comparing the calculated body temperature with the reference value associated with the group to which the thermal image data belongs. Here, the change detection section 307 determines that there is a change in body temperature if a temperature difference between the calculated body temperature and the normal body temperature indicated as the reference value is equal to or larger than plus or minus one degree Celsius.

In the example of FIG. 6, the classification data 311B are divided into the first to Nth groups depending on the position and the depth. Accordingly, there are also N reference values associated with the first to Nth groups.

In the present embodiment, as the reference value, a value calculated in the learning phase is employed. However, the present disclosure is not limited thereto, and a value determined in advance may alternatively be employed for each group. Alternatively, as the reference value, a value calculated for each group from thermal image data classified during a certain period of time from present to past may be employed.

Figure 7:
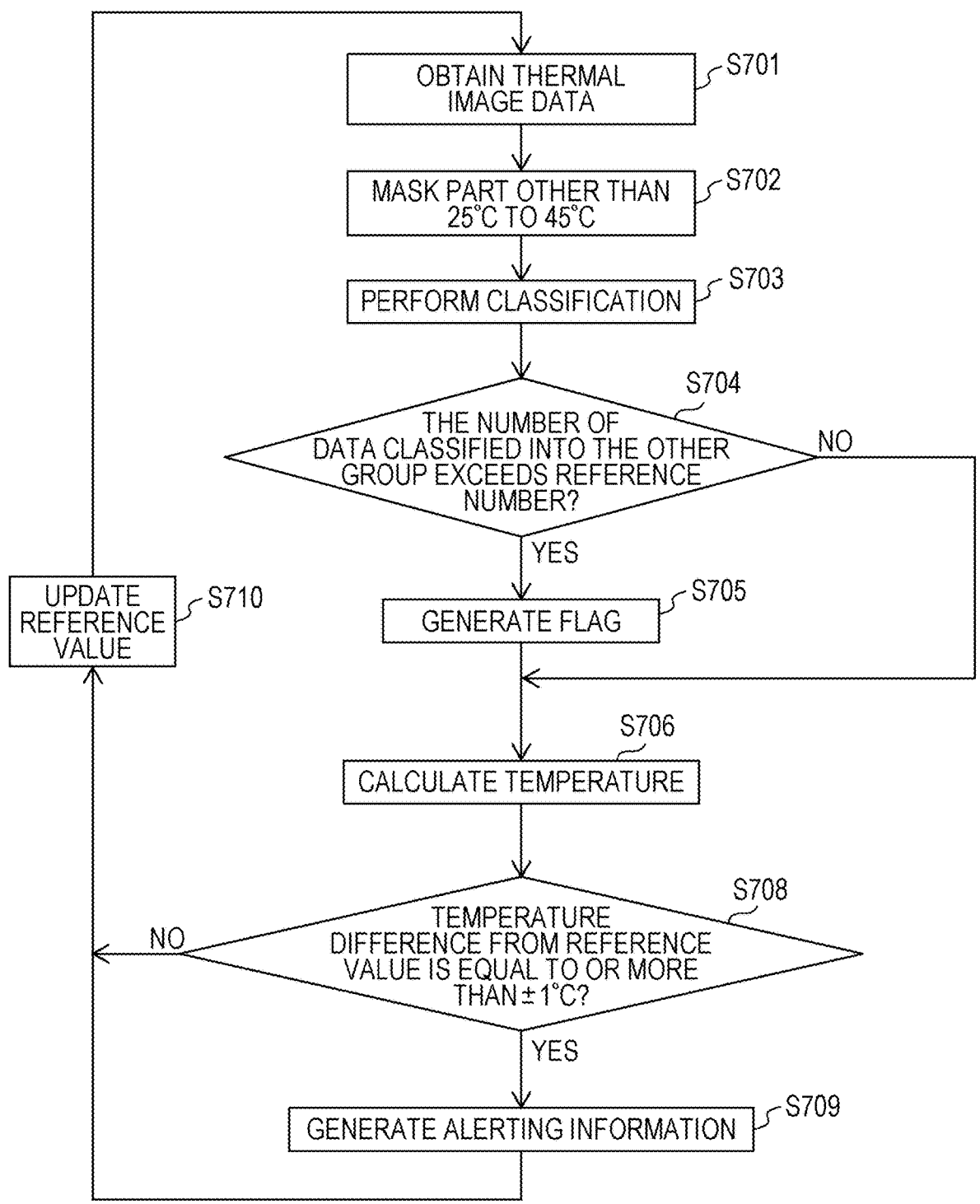
FIG. 7 is a flowchart illustrating one example of a process of an information processing device in the detection phase.

FIG. 7 is a flowchart illustrating one example of a process of the information processing device 102 in the detection phase. For example, the flowchart of FIG. 7 is executed periodically at a predetermined sampling frequency at which the sensing section 101A obtains thermal image data.

First, the data classification section 305 obtains thermal image data to which time data is assigned by the time data assignment section 304 (S701). Next, the data classification section 305 performs the mask process on the obtained thermal image data to mask part other than 25 degrees Celsius to 45 degrees Celsius (S702).

Next, the data classification section 305 classifies the thermal image data subjected to the mask process by inputting the thermal image data subjected to the mask process to the neural network for which the classification parameters 311A are generated in the learning phase (S703). This allows thermal image data to be classified into one of the first to Nth groups according to the position and the depth. It is possible that thermal image data cannot be classified to any one of the first to Nth groups. For example, it is a case where the human body 106 takes a position and a depth in the detection phase, which have not been taken in the learning phase. In this case, this thermal image data is classified to an "other group".

Next, the data classification section 305 determines whether or not the number of pieces of thermal image data classified to the other group exceeds a reference number (S704).

If the number of pieces of thermal image data classified to the other group exceeds the reference number (Yes in S704), a flag is generated to prompt re-execution of the learning phase (S705). Here, for example, the generated flag is transmitted to the information display section 103A. The information display section 103A displays an image indicating generation of a flag on the display section 310. This prompts the manager to execute the learning phase again. The manager inputs, for example, a re-learning command to the information processing section 102A using an input device not illustrated in the figure. Then, the data classification section 305 executes the foregoing learning phase using all the thermal image data accumulated as the classification data 311B to date, and generates the classification parameters 311A again. This allows new learning to be executed on a group including a position and a depth of the human body 106 indicated by the thermal image data classified to the other group. As a result, a group based on the position and the depth of the human body 106 taken for the first time in the detection phase is added as a classification target group. Note that, when the learning phase is re-executed, reference values of the respective groups are calculated from thermal image data classified into the respective groups. Thus, with regard to thermal image data classified to the newly added group, a temperature change is detected by comparing the thermal image data with a corresponding reference value.

Next, the change detection section 307 detects part designated by the comparison part parameter 311C from thermal image data being a detection target, and calculates the body temperature of the human body 106 using the pixel value at the detected part (S706).

Next, the change detection section 307 compares the reference value associated with the group of the thermal image data being a detection target with the body temperature of the human body 106 calculated in step S706, and generates alerting information (S709) if the temperature difference between the body temperature of human body 106 and the reference value is equal to or larger than plus or minus one degree Celsius (Yes in S708). When step S709 ends, the process proceeds to step S710. The generated alerting information is transmitted to the information display section 103A, and an alert is issued to the manager. On the other hand, if the temperature difference between the body temperature of the human body 106 and the reference value is less than plus or minus one degree Celsius (No in S708), the process proceeds to step S710.

In step S710, using the classification data 311B to which thermal image data being a detection target is classified, the data management section 306 updates the reference value of the group to which the thermal image data belongs, and the process returns to step S701. For example, if the thermal image data being a detection target is classified to the first group, the data management section 306 may update the reference value of the first group.

As described above, according to the information processing device 102 of Embodiment 1, an abnormal body temperature of the human body 106 is detected by classifying thermal image data into the groups based on the position and the depth and comparing the reference value associated with the group with the body temperature calculated from the thermal image data. Accordingly, the information processing device 102 enables precise detection of presence or absence of abnormal body temperature of the human body 106 regardless of the position and the depth of the human body 106 at the time of measurement. Further, the information processing device 102 enables measurement of the body temperature of the human body 106 without contact, thereby making it possible to detect abnormal body temperature without placing burden on both the human body 106 and the manager of the human body 106. Further, in the present embodiment, the reference value is calculated from thermal image data obtained by capturing an image of the human body 106. This enables calculation of a reference value appropriate for the human body 106.

Embodiment 2

Figure 8:
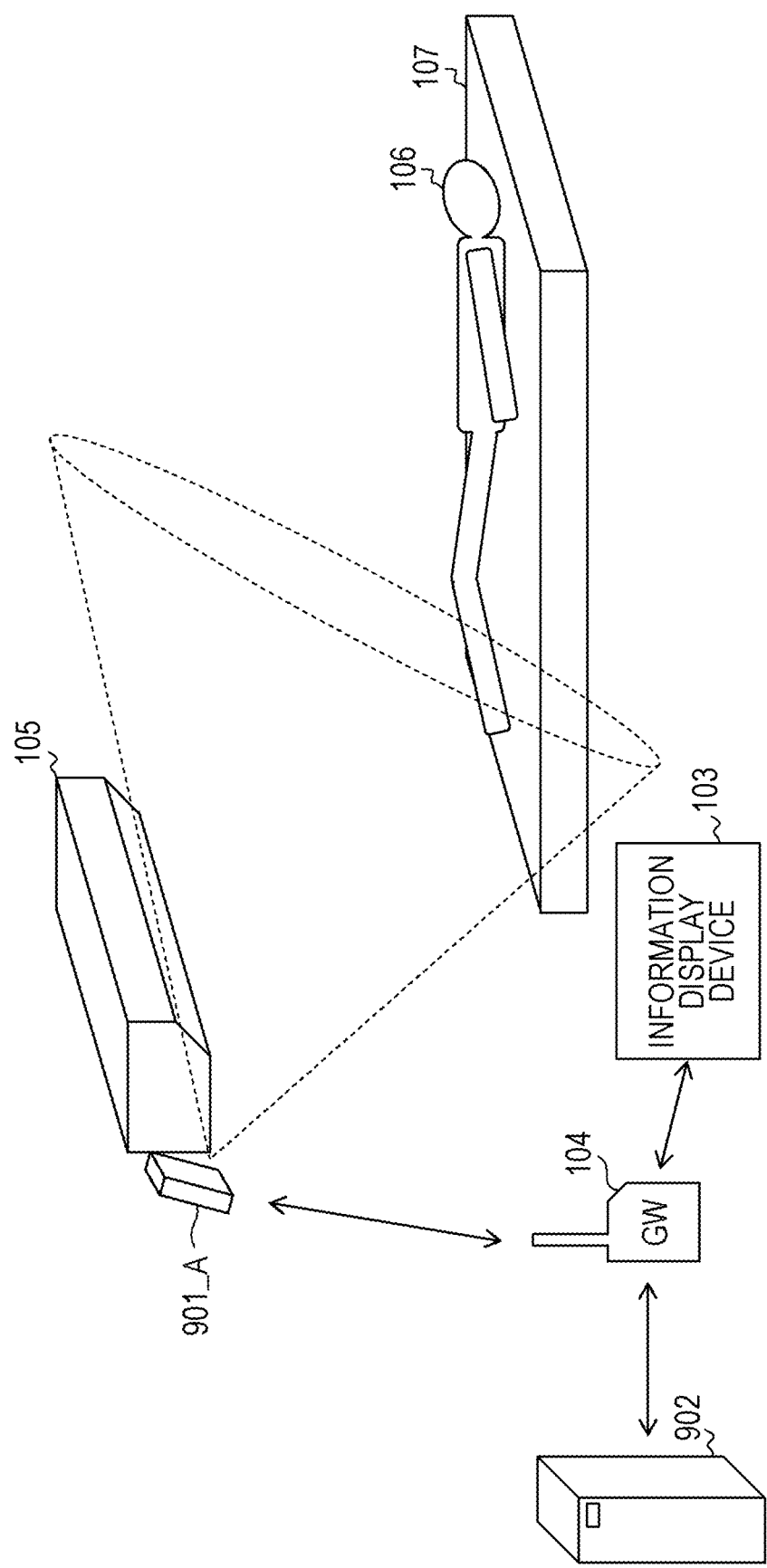
FIG. 8 is a diagram illustrating an overview of a biological information sensing device to which an information processing device according to Embodiment 2 is applied.

FIG. 8 is a diagram illustrating an overview of a biological information sensing device to which an information processing device according to Embodiment 2 is applied. The biological information sensing device according to Embodiment 2 employs a sensing device 901_A including a radio wave sensor. In the present embodiment, no description is provided for a constituting element identical to that of Embodiment 1.

The sensing device 901_A includes a radio wave sensor and is installed inside a room such as a bedroom or the like, as in FIG. 1. Here, for example, the sensing device 901_A is installed in a room in such a way that the measurement range of the sensing device 901_A covers the entire area of the bed 107. The sensing device 901_A obtains activity amount data of the human body 106. The sensing device 901_A transmits the obtained activity amount data to an information processing device 902 via a GW 104. The information processing device 902 classifies the activity amount data into respective groups based on the position of the human body 106 and manages the classified activity amount data.

Upon detecting a change in activity amount (one example of the biological information) of the human body 106 by comparing activity amount data classified into respective groups and activity amount data measured in this time, the information processing device 902 notifies the information display device 103 of alerting information indicating abnormal activity amount of the human body 106 via the GW 104. Upon receipt of the alerting information, the information display device 103 issues an alert. This enables the manager of the human body 106 to aware abnormal activity amount of the human body 106.

Figure 9:
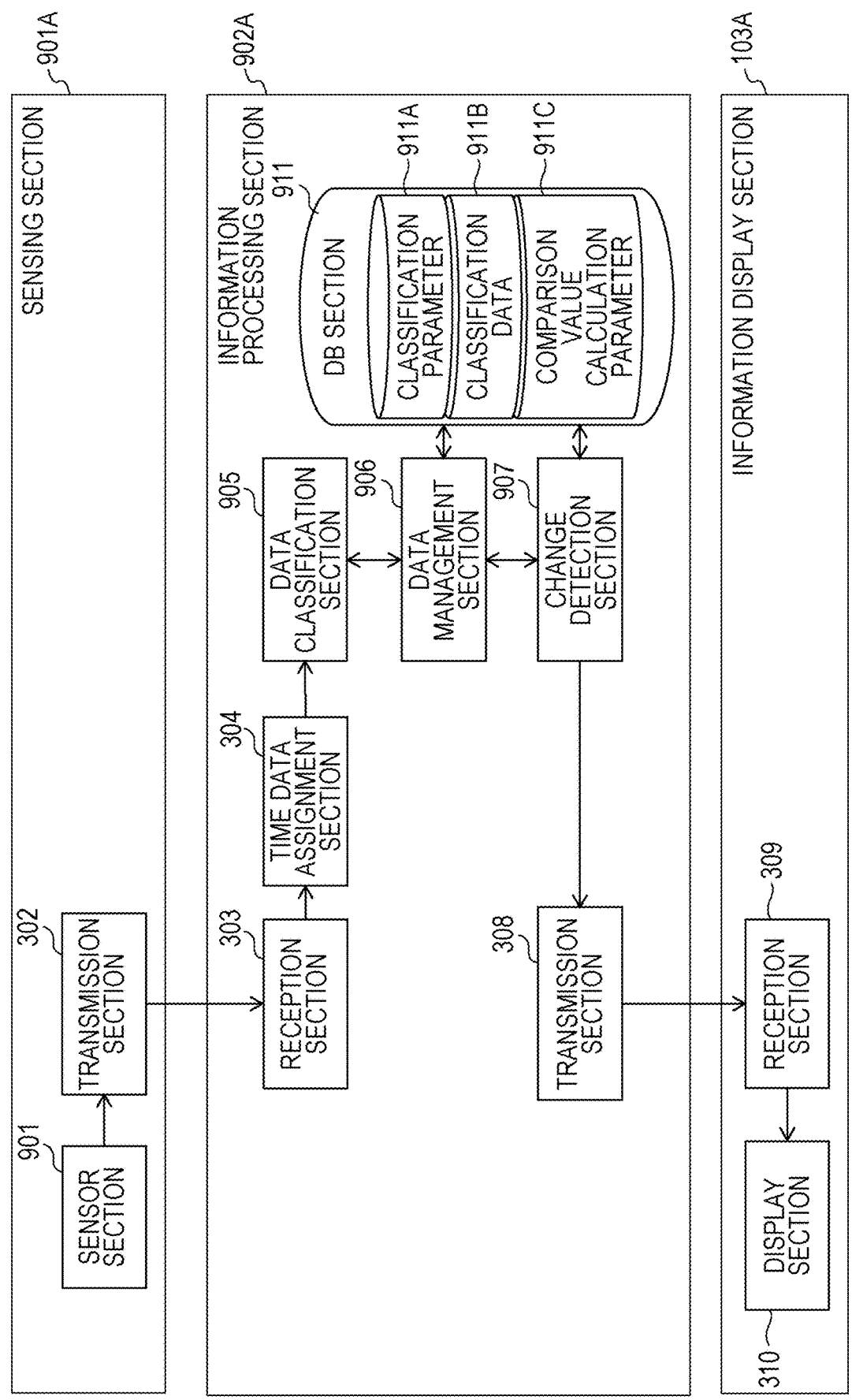
FIG. 9 is a diagram illustrating one example of a functional configuration of a biological information sensing device to which an information processing device according to Embodiment 2 is applied.

FIG. 9 is a diagram illustrating one example of a functional configuration of a biological information sensing device to which an information processing device according to Embodiment 2 is applied. The biological information sensing device includes a sensing section 901A (one example of the sensor) corresponding to the sensing device 901_A, an information processing section 902A corresponding to the information processing device 902, and an information display section 103A corresponding to the information display device 103. The sensing section 901A differs from that of FIG. 3 in that the sensing section 901A includes a sensor section 901.

The sensor section 901 is constituted by, for example, a two-channel Doppler-type radio wave sensor, and obtains activity amount data of the human body 106 by emitting a radio wave to the human body 106 at predetermined sampling intervals and receiving a return wave from the human body 106. As the radio wave, for example, a microwave in a 24 GHz band may be employed.

Alternatively, as the sensor section 901, a radio wave sensor other than that of Doppler type may be employed. For example, a radio wave sensor of Frequency Modulated Continuous Wave (FMCW) type and the like may be employed.

In the learning phase, the data classification section 905 learns about groups based on the position of the human body 106 by obtaining a plurality of pieces of activity amount data to which time data is assigned by the time data assignment section 304 and classifying the obtained plurality of pieces of activity amount data based on waveform information.

In the case where the sensor section 901 is constituted by a two-channel Doppler-type radio wave sensor, the distance to the human body 106 varies depending on the amplitude of activity amount data, and the speed of body motion varies depending on the change in frequency of the activity amount data. Accordingly, in this case, as the waveform information, the amplitude and the frequency are employed.

In the case where the sensor section 901 is constituted by a FMCW-type radio wave sensor, the distance to the human body 106 varies depending on the amplitude and the phase of activity amount data, and the speed of body motion varies depending on the change in phase of the activity amount data. Accordingly, in this case, as the waveform information, the amplitude and the phase are employed.

Further, the speed of body motion changes depending on the position of the human body 106 such as lying on one's back, lying on one's stomach, or lying on one's side, and the speed of body motion varies depending on the state of the human body 106 such as being asleep or being awake. Accordingly, classifying activity amount data based on the waveform information enables to classify the activity amount data into respective groups of the position, the state, and the distance of the human body 106, thereby enabling learning about the group for each position, state, and distance of the human body 106.

In the present embodiment, the data classification section 905 may learn about the groups using the machine learning described in Embodiment 1.

In the detection phase where a change in biological information is detected, the data classification section 905 classifies, to one of the groups learned in the learning phase, activity amount data to which time data is assigned by the time data assignment section 304 based on the waveform information. Specifically, the data classification section 905 may classify activity amount data by inputting the activity amount data to a neural network generated in the learning phase.

In the learning phase, the data management section 906 calculates, as a reference value of each group, a representative value of activity amount for each of the groups from the activity amount data classified into each group by the data classification section 905. Here, as the reference value, reference values of a body motion value, a heart rate, and a breathing rate can be employed. With regard to the activity amount data, frequency bands of the body motion value, the heart rate, and the breathing rate are known in advance. Thus, the body motion value, the heart rate, and the breathing rate can be detected from values of the respective frequency bands. Accordingly, the data management section 906 may calculate an average value of each group of the body motion values, the heart rates, and the breathing rates, as the reference value of each group of the body motion values, the heart rates, and the breathing rates. The data management section 306 may update the reference value based on a classification result of activity amount data even in the detection phase.

The change detection section 907 detects presence or absence of a change in activity amount of the human body 106 by, in the detection phase, calculating an activity amount including a body motion value, a breathing rate, and a heart rate of the human body 106 from the activity amount data classified to one of the groups by the data classification section 905 and comparing the calculated body temperature with the reference value associated with the group to which the thermal image data belongs. Further, when a change in activity amount is detected, the change detection section 907 generates alerting information indicating abnormal activity amount. Here, it is assumed that the reference value corresponds to an activity amount of the human body 106 in normal times. Thus, the change detection section 907 may determine that there is a change in activity amount if a difference between the reference value and the activity amount indicated by a target activity amount data is equal to or larger than a plus or minus a predetermined value.

The DB section 911 stores therein classification parameters 911A, classification data 911B, and comparison value calculation parameters 911C. The classification parameters 911A are, for example, weight coefficients of a neural network obtained as a result of learning of activity amount data in the learning phase. The comparison value calculation parameter 911C is a parameter defining content of a comparison value to be detected from activity amount data at the time of detection by the change detection section 907. In the present embodiment, the body motion value, the pulse rate, and the heart rate are employed as the reference values. Thus, as the comparison value calculation parameter 911C, for example, information indicating each of the body motion value, the pulse rate, and the heart rate is employed. Alternatively, as the comparison value calculation parameter 911C, for example, a frequency band in activity amount data for each of the body motion value, the pulse rate, and the heart rate may be employed.

In the case where supervised machine learning is employed, the DB section 911 may store therein information relating to groups being classification targets determined in advance (information indicating position (lying on one's back, lying on one's stomach, or the like), state (being asleep, being awake, or the like), distance).

Figure 10:
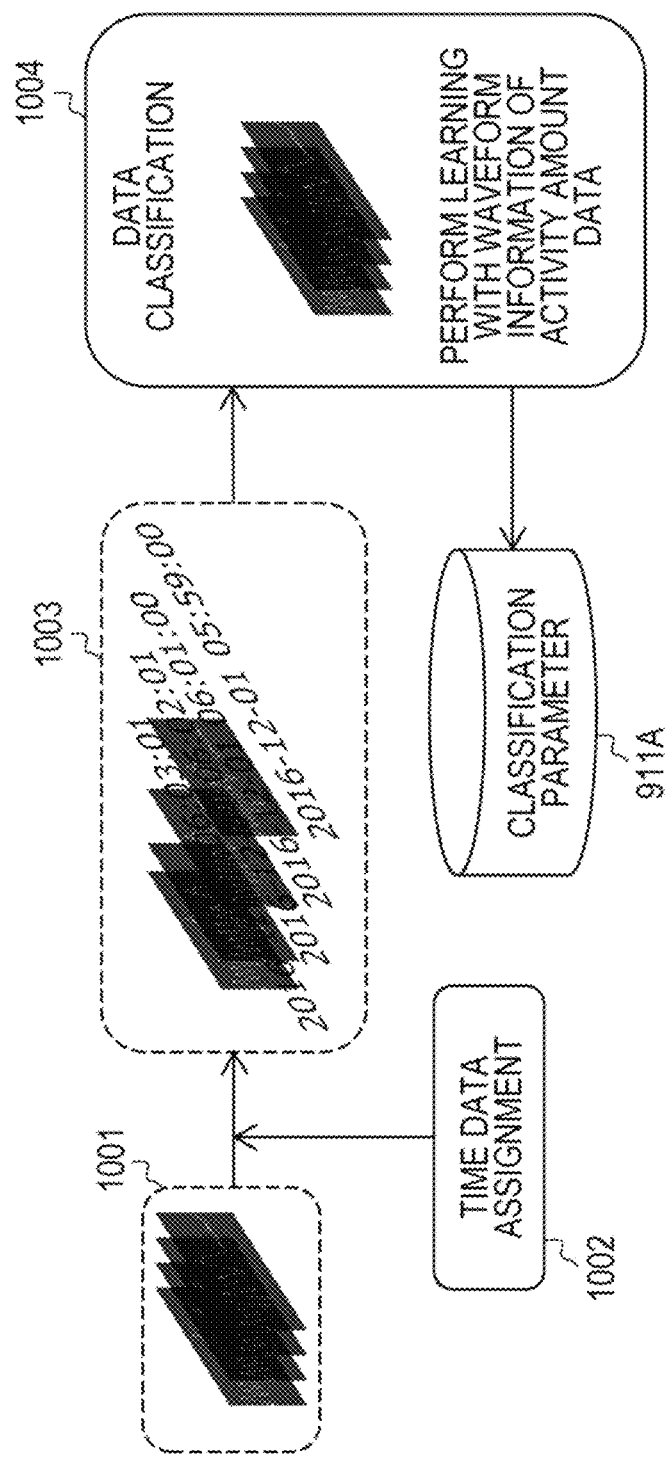
FIG. 10 is a diagram illustrating a data processing method in a learning phase.
Figure 11:
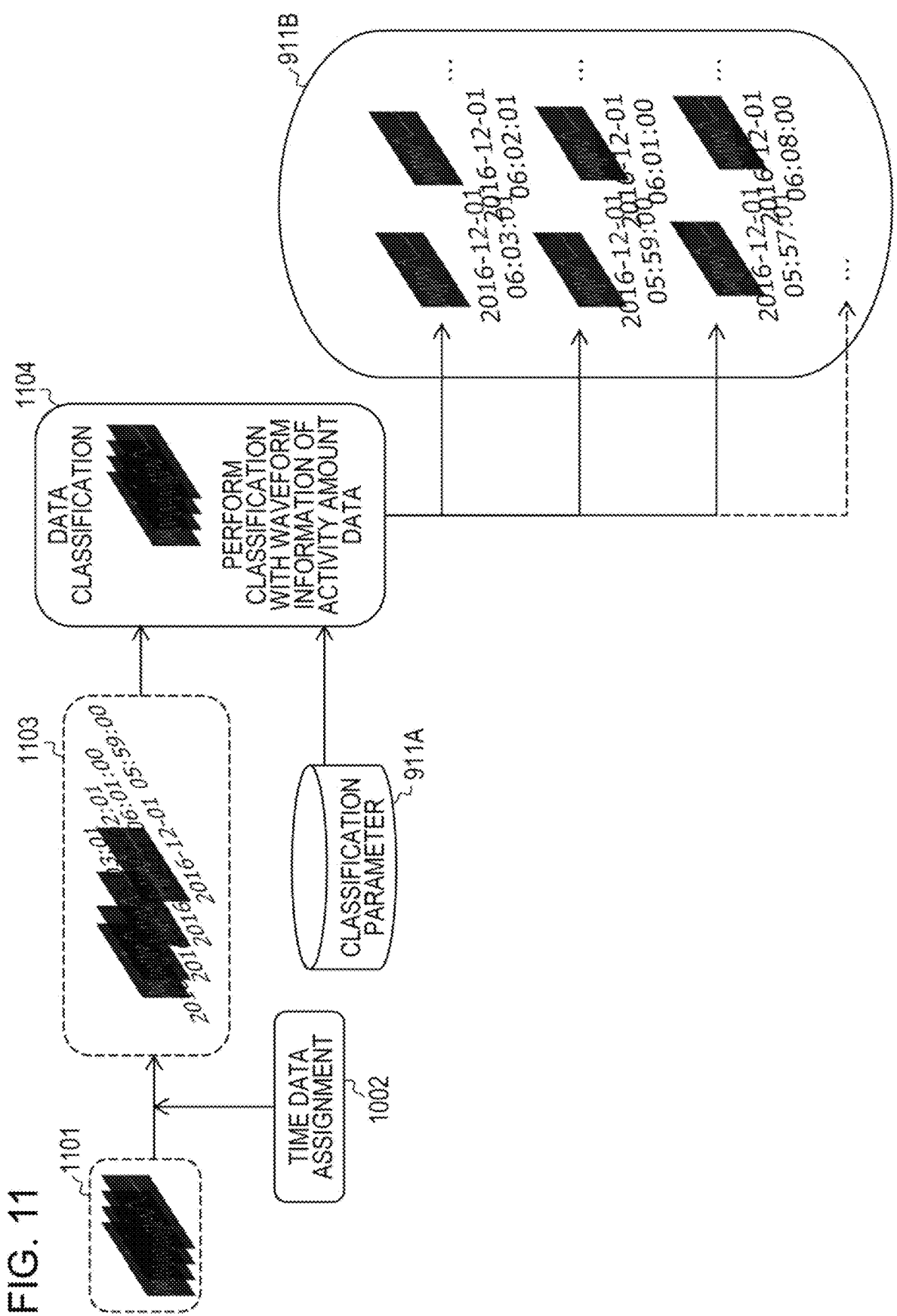
FIG. 11 is a diagram illustrating a data processing method in a detection phase.
Figure 12:
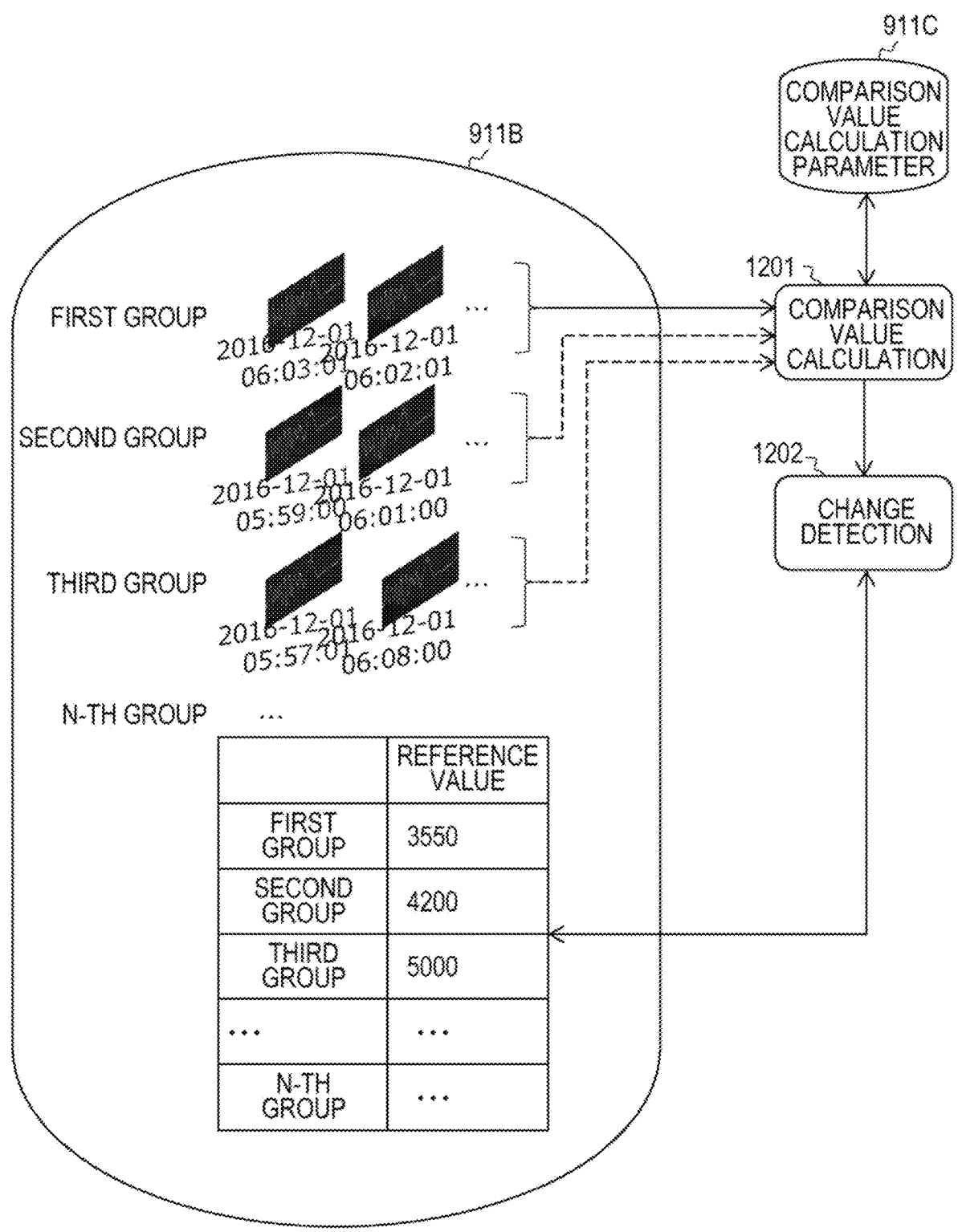
FIG. 12 is a diagram that follows FIG. 11 and illustrates the data processing method in the detection phase.

Next, a data processing method in the information processing section 902A is described with reference to FIG. 10 to FIG. 12. FIG. 10 is a diagram illustrating the data processing method in the learning phase. FIG. 11 is a diagram illustrating the data processing method in the detection phase. FIG. 12 is a diagram that follows FIG. 11 and illustrates the data processing method in the detection phase.

Referring to FIG. 10, when the biological information sensing device is installed in a site, the information processing section 902A generates the classification parameters 911A by learning activity amount data. First, the time data assignment section 304 assigns time data (1002) to each of activity amount data (1001) obtained by the sensing section 901A.

Next, by performing machine learning using a neural network, the data classification section 905 classifies the activity amount data (1003), to which time data is assigned, into the groups and generates the classification parameters 911A (1004).

Next, referring to FIG. 11, when the learning phase ends, the detection phase starts. As in the learning phase, the time data assignment section 304 assigns time data (1002) to activity amount data (1101) obtained by the sensing section 901A. Next, as in the learning phase, by inputting, to the neural network generated in the learning phase, the activity amount data (1103) to which time data is assigned, the data classification section 905 classifies the activity amount data into one of the groups having been classified in the learning phase (1104). In this way, the detection-target activity amount data is classified according to waveform information. The classified activity amount data is stored in the DB section 911 as the classification data 911B.

Next, referring to FIG. 12, the change detection section 907 reads activity amount data, which becomes a detection target, from the classification data 911B, and detects a comparison value designated by the comparison value calculation parameter 911C from the read activity amount data (1201). Here, as the comparison value, the body motion value, the pulse rate, and the heart rate are employed. Accordingly, a body motion value, a pulse rate, and a heart rate are extracted from the read activity amount data.

Next, the change detection section 907 detects presence or absence of a change in activity amount of the human body 106 (1202) by comparing the body motion value, the pulse rate, and the heart rate detected from the activity amount data with the respective reference values associated with the group to which the activity amount data is classified. Here, the change detection section 907 determines that there is a change in activity amount if each of differences between the detected body motion value, pulse rate, and heart rate and their respective reference values is equal to or larger than plus or minus a predetermined value.

In the example of FIG. 12, the classification data 911B is classified into N groups consisting of the first to Nth groups (N is an integer equal to or larger than one). Accordingly, there are also N reference values associated with the first group to the Nth group. Although, in the example of FIG. 12, a reference value for one of the body motion value, the heart rate, and the pulse rate is illustrated in the figure as the reference value, reference values for respective ones of the body motion value, the heart rate, and the pulse rate are included in an actual case.

In the present embodiment, as the reference value, a value calculated in the learning phase is employed. However, the present disclosure is not limited thereto, and a value determined in advance may alternatively be employed for each group. Alternatively, as the reference value, a value calculated from activity amount data classified during a certain period of time from present to past may be employed.

In Embodiment 2, the flowchart is the same as that of FIG. 7 except that the thermal image data is replaced with the activity amount data. Thus, the description thereof is not repeated.

As described above, in Embodiment 2, an abnormal activity amount is detected by classifying activity amount data into each group including the position, the state, and the distance according to waveform information of the activity amount data, and comparing an activity amount of the classified activity amount data with the reference value of the associated group. Accordingly, in Embodiment 2, presence or absence of abnormal activity amount of the human body 106 can be detected precisely regardless of the position of the human body 106 at the time of measurement. Further, according to the present aspect, the biological information is measured without contact. This enables detection of abnormal activity amount without placing burden on both the human body 106 and a measurement operator.

The information processing device according to the present disclosure may adopt the following modified examples.

Modified Example 1

The change detection section 307 may determine whether or not measurement data is the measurement data measured at predetermined time of day based on time data assigned to the measurement data, and performs a process for detecting a change if the measurement data is the measurement data measured at the predetermined time of day. Here, as the predetermined time of day, the time of day at which the activity amount of the human body 106 is stable is employed. For example, a certain period immediately after waking up, a certain period immediately before waking up, a certain period immediately before going to bed, or a certain period immediately after falling to sleep may be employed.

In this case, the data classification section 305 may classify only measurement data measured at the predetermined time of day. In this way, the reference value becomes a value calculated from the measurement data of the predetermined time of day. This enables precise detection of a change in biological information.

Alternatively, the data classification section 305 may classify measurement data while considering time of day, in addition to the position, the state, or the distance. In this case, a change in biological information can be detected precisely in consideration of the activity amount of the human body 106, which varies depending on time of day.

Modified Example 2

Figure 13:
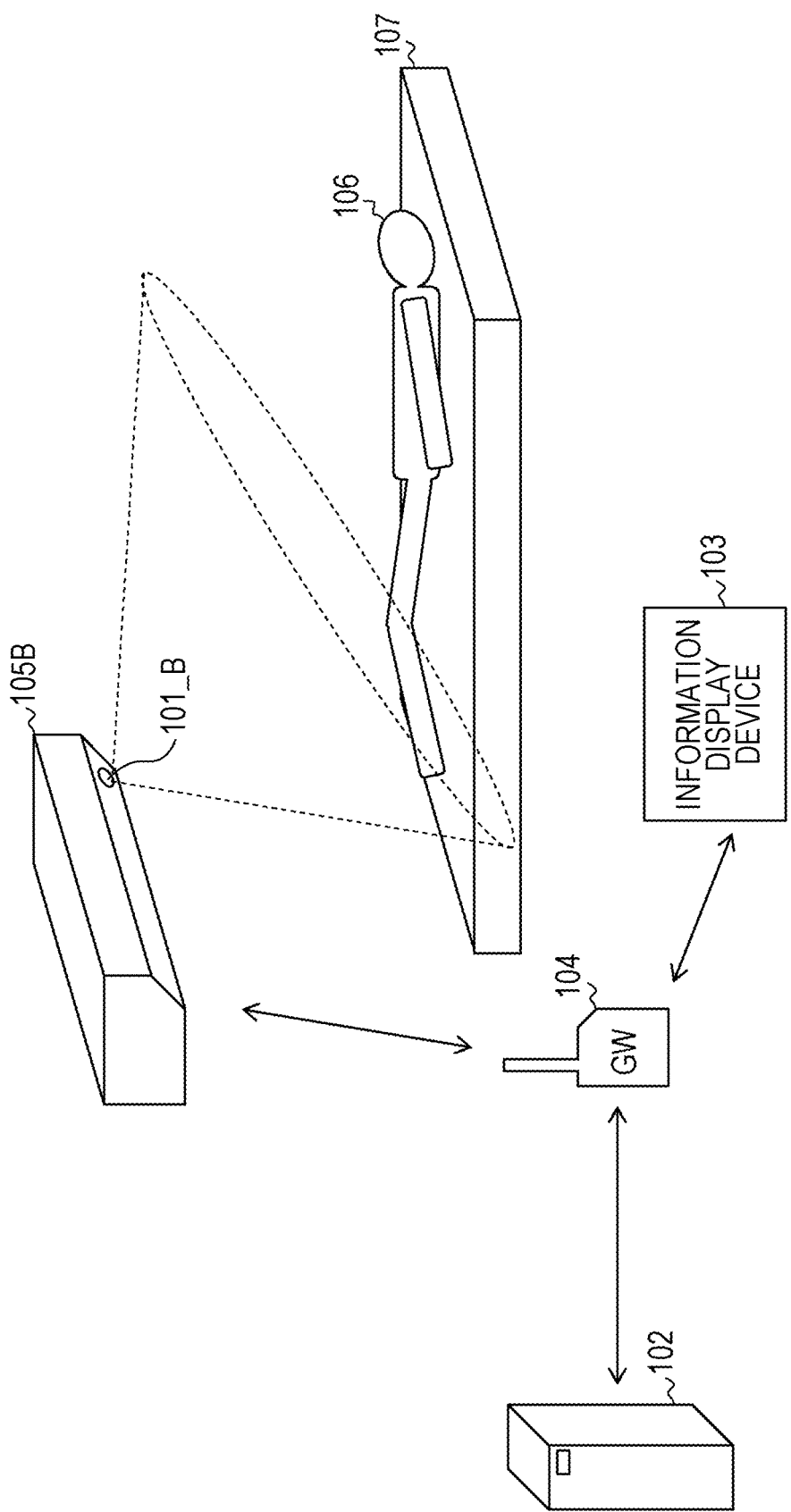
FIG. 13 is a diagram illustrating an overview of a biological information sensing device to which an information processing device according to a modified example 2 of the present disclosure is applied.

FIG. 13 is a diagram illustrating an overview of a biological information sensing device to which an information processing device according to a modified example 2 of the present disclosure is applied. In Embodiment 1, as illustrated in FIG. 1, the sensing device 101 is configured as a unit separated from the air conditioner 105. However, in the modified example 2, as illustrated in FIG. 13, a sensing device 101_B is included in an air conditioner 105B. In the example of FIG. 13, the sensing device 101_B is installed on the front face of the air conditioner 105B in such a way that a sensor face faces the human body 106.

In the modified example 2, the information processing device 102 may be, for example, constituted by a cloud server or by a server installed in a local place.

Modified Example 3

Figure 14:
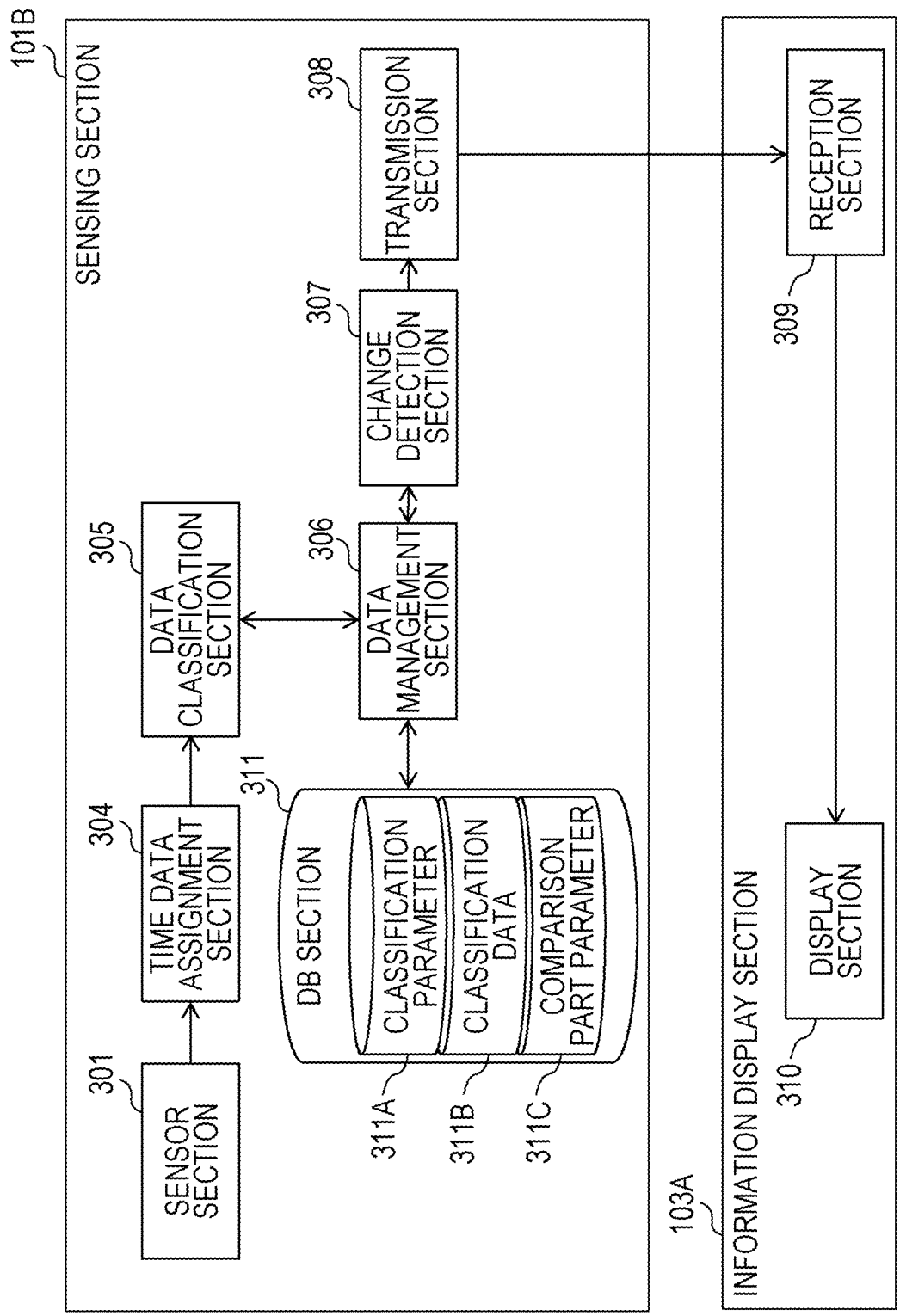
FIG. 14 is a diagram illustrating a configuration of functions of a biological information sensing device to which an information processing device according to a modified example 3 of the present disclosure is applied.

FIG. 14 is a diagram illustrating a configuration of functions of a biological information sensing device to which an information processing device according to a modified example 3 of the present disclosure is applied. In Embodiment 1, the information processing section 102A is configured as a unit separated from the sensing section 101A. However, in the modified example 3, as illustrated in FIG. 14, the sensing section 101B and the information processing section 102A illustrated in FIG. 3 are configured as a unified unit. In the modified example 3, the information processing device is constituted by the sensing section 101B.

In the modified example 3, the sensing section 101A and the information processing section 102A are unified. Thus, the transmission section 302 and the reception section 303 that are present in FIG. 3 are omitted. In the modified example 3, the sensing section 101B may be constituted by a sensor unit built inside the air conditioner 105 or a dedicated sensor unit provided in a unit separated from the air conditioner 105.

Figure 15:
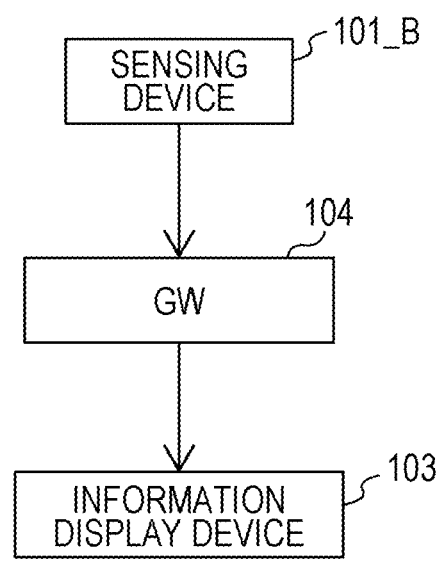
FIG. 15 is a diagram illustrating one example of a connection configuration of a biological information sensing device to which an information processing device according to the modified example 3 of the present disclosure is applied.

FIG. 15 is a diagram illustrating one example of a connection configuration of a biological information sensing device to which an information processing device according to the modified example 3 of the present disclosure is applied. A sensing device 101_B corresponds to the sensing section 101B illustrated in FIG. 14. The sensing device 101_B is connected to the information display device 103 via the GW 104.

Modified Example 4

Figure 16:
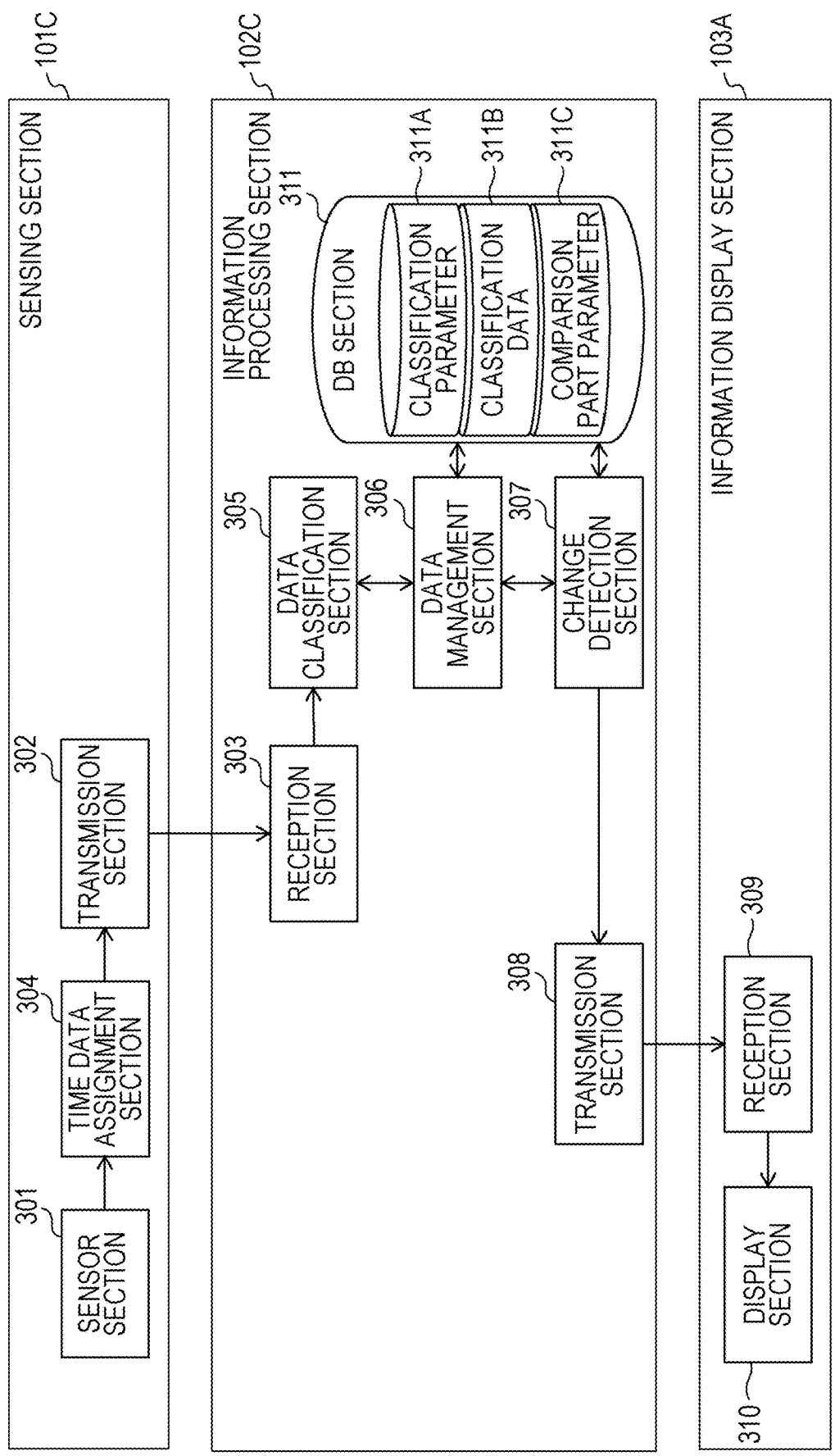
FIG. 16 is a diagram illustrating a configuration of functions of a biological information sensing device to which an information processing device according to a modified example 4 of the present disclosure is applied.

FIG. 16 is a diagram illustrating a configuration of functions of a biological information sensing device to which an information processing device according to a modified example 4 of the present disclosure is applied. In Embodiment 1, the time data assignment section 304 is provided in the information processing section 102A. However, in the modified example 4, the time data assignment section 304 is provided in a sensing section 101C. The time data assignment section 304 is arranged between the sensor section 301 and the transmission section 302. On the other hand, an information processing section 102C does not include the time data assignment section 304. In the modified example 4, a process for assigning time data is performed in the sensing section 101C, thereby reducing processing load of the information processing section 102C. In the modified example 4, the sensing section 101C is constituted by a high-performance sensor built inside the air conditioner 105 or by a high-performance sensor configured as a unit separated from the air conditioner 105.

Modified Example 5

Figure 17:
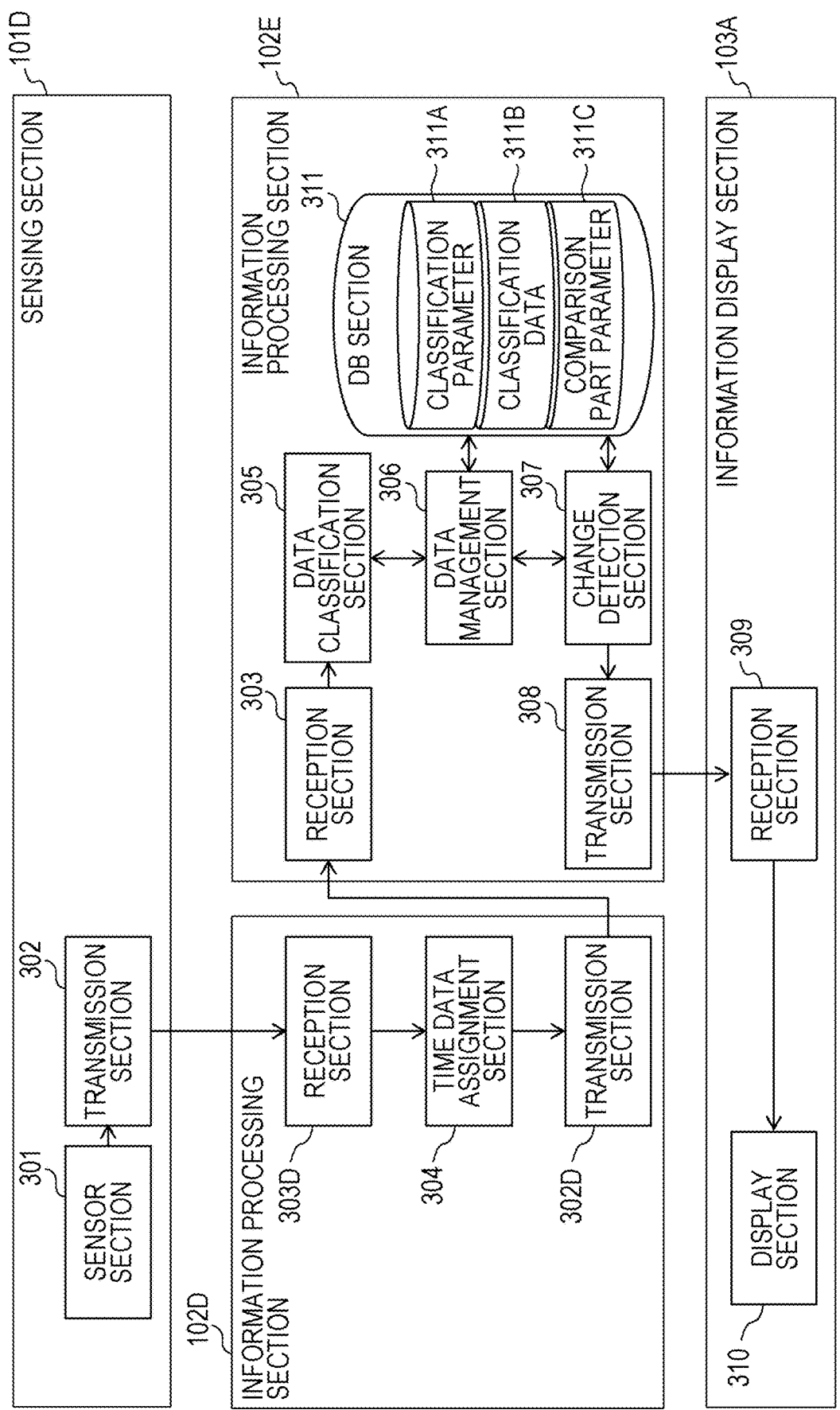
FIG. 17 is a diagram illustrating a configuration of functions of a biological information sensing device to which an information processing device according to a modified example 5 of the present disclosure is applied.

FIG. 17 is a diagram illustrating a configuration of functions of a biological information sensing device to which an information processing device according to a modified example 5 of the present disclosure is applied. In the example of FIG. 17, the information processing section 102A is divided into an information processing section 102D including the time data assignment section 304 and an information processing section 102E.

Figure 18:
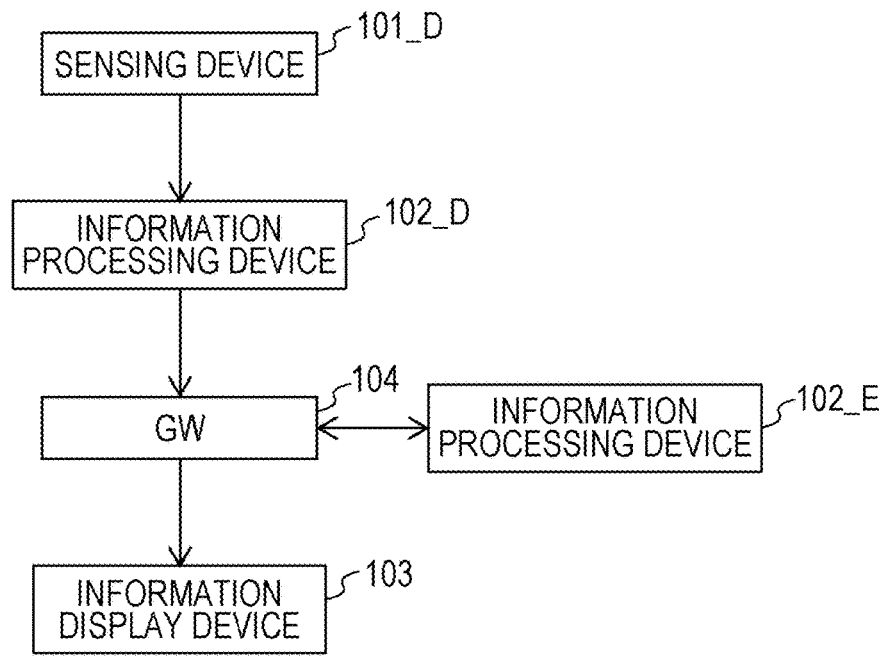
FIG. 18 is a diagram illustrating a first example of a connection configuration of a biological information sensing device to which an information processing device according to the modified example 5 of the present disclosure is applied.

The information processing section 102D is constituted by, for example, a high-performance sensor built in the air conditioner 105 or a computer for home use. The information processing section 102E is constituted by, for example, a cloud server. The information processing section 102D includes a reception section 303D for communicating with a sensing section 101D and a transmission section 302D for communicating with the information processing section 102E. The information processing section 102E includes the reception section 303 for communicating with the information processing section 102D. FIG. 18 is a diagram illustrating a first example of a connection configuration of a biological information sensing device to which an information processing device according to the modified example 5 of the present disclosure is applied. An information processing device 102_D corresponding to the information processing section 102D is connected to an information processing device 102_E corresponding to the information processing section 102E and the information display device 103 via the GW 104. The information processing device 102_D is also connected to a sensing device 101_D corresponding to the sensing section 101D.

Figure 19:
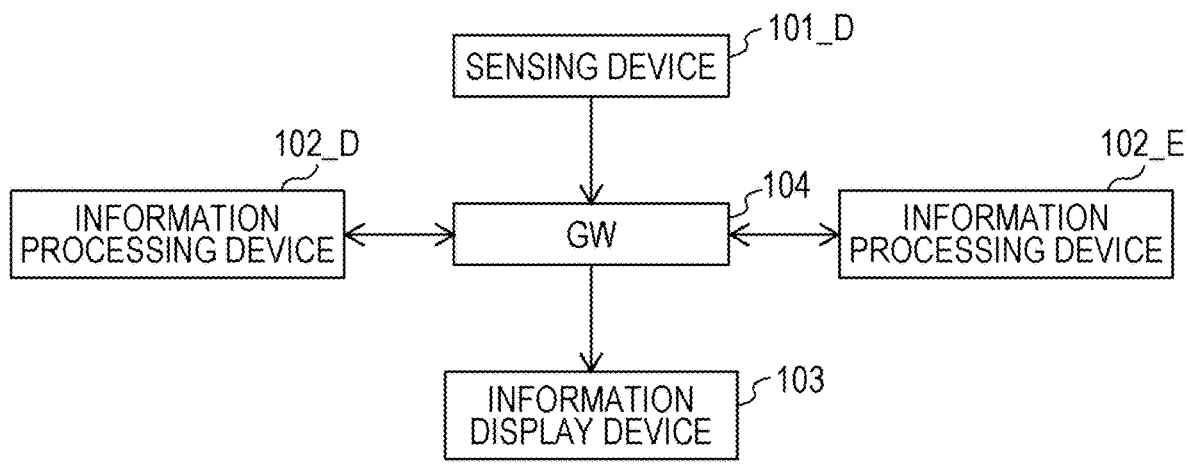
FIG. 19 is a diagram illustrating a second example of a connection configuration of a biological information sensing device to which an information processing device according to the modified example 5 of the present disclosure is applied.

FIG. 19 is a diagram illustrating a second example of the connection configuration of a biological information sensing device to which an information processing device according to the modified example 5 of the present disclosure is applied. In the second example, the sensing device 101_D, the information processing device 102_D, the information processing device 102_E, and the information display device 103 are connected to each other via the GW 104.

Modified Example 6

Figure 20:
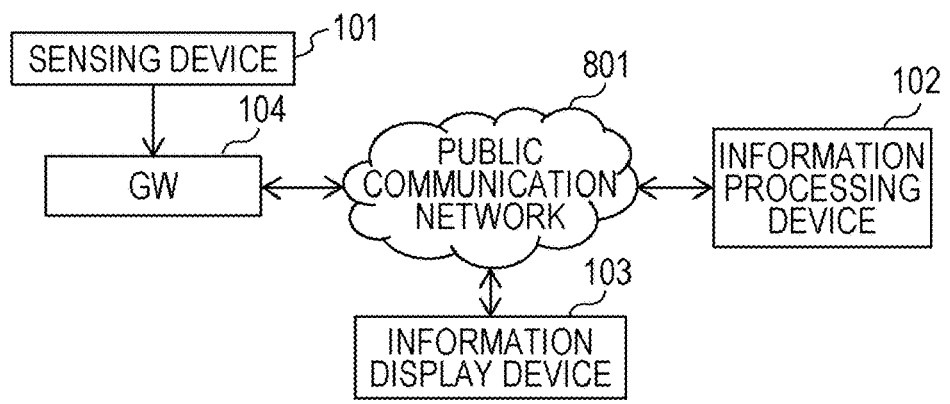
FIG. 20 is a diagram illustrating a connection configuration of a biological information sensing device to which an information processing device according to a modified example 6 of the present disclosure is applied.

FIG. 20 is a diagram illustrating a connection configuration of a biological information sensing device to which an information processing device according to a modified example 6 of the present disclosure is applied. In the modified example 6, the GW 104 is connected to the information processing device 102 and the information display device 103 via a public communication network 801. The sensing device 101 is connected to the GW 104.

Modified Example 7

Figure 21:
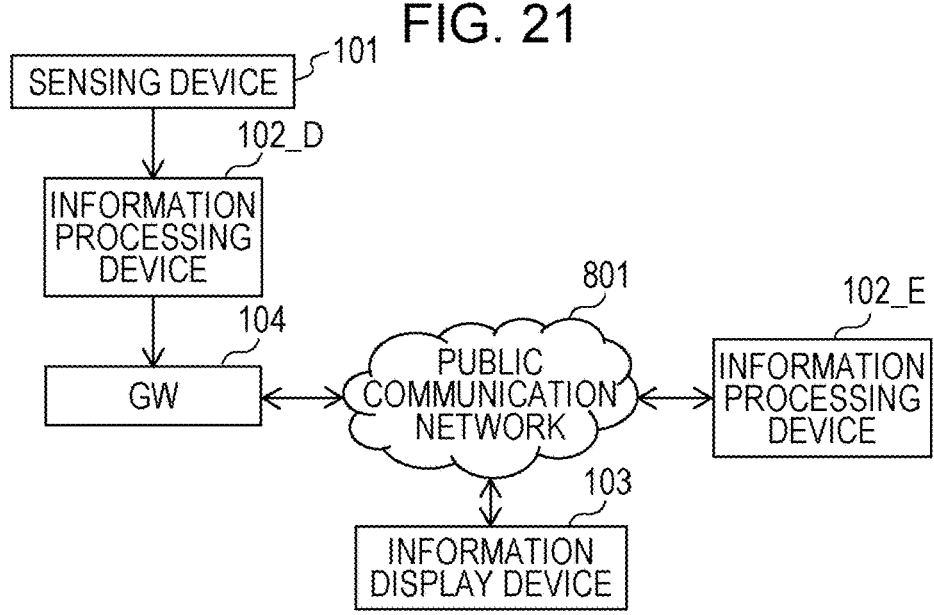
FIG. 21 is a diagram illustrating a connection configuration of a biological information sensing device to which an information processing device according to a modified example 7 of the present disclosure is applied.

FIG. 21 is a diagram illustrating a connection configuration of a biological information sensing device to which an information processing device according to a modified example 7 of the present disclosure is applied. The modified example 7 is an example in which the biological information sensing device according to the modified example 5 is configured using the public communication network 801. The GW 104 is connected to the information processing device 102_E and the information display device 103 via the public communication network 801. The sensing device 101 is connected to the GW 104 via the information processing device 102_D.

Modified Example 8

Figure 22:
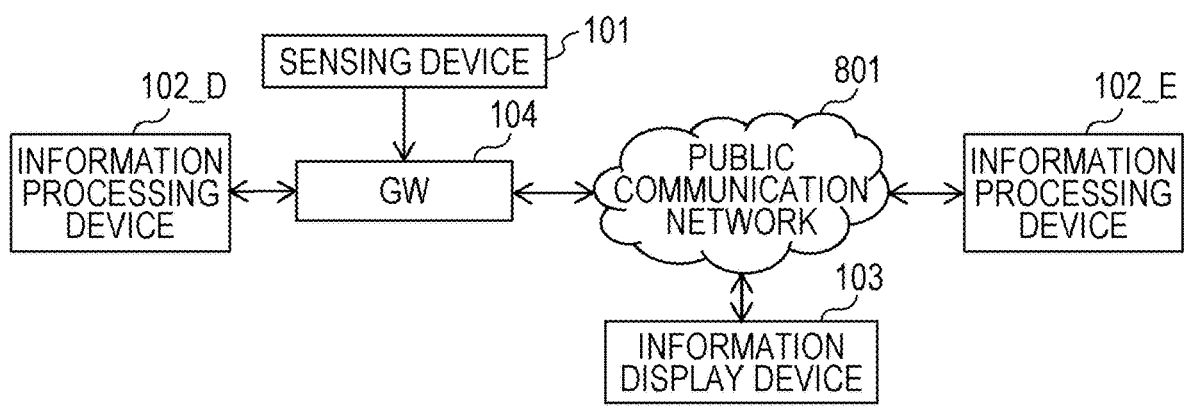
FIG. 22 is a diagram illustrating a connection configuration of a biological information sensing device to which an information processing device according to a modified example 8 of the present disclosure is applied.

FIG. 22 is a diagram illustrating a connection configuration of a biological information sensing device to which an information processing device according to a modified example 8 of the present disclosure is applied. The modified example 8 is an example in which the biological information sensing device according to the modified example 5 is configured using the public communication network 801.

The GW 104 is connected to the information processing device 102_E and the information display device 103 via the public communication network 801. Each of the sensing device 101 and the information processing device 102_D is connected to the GW 104 via a LAN.

Modified Example 9

Figure 23:
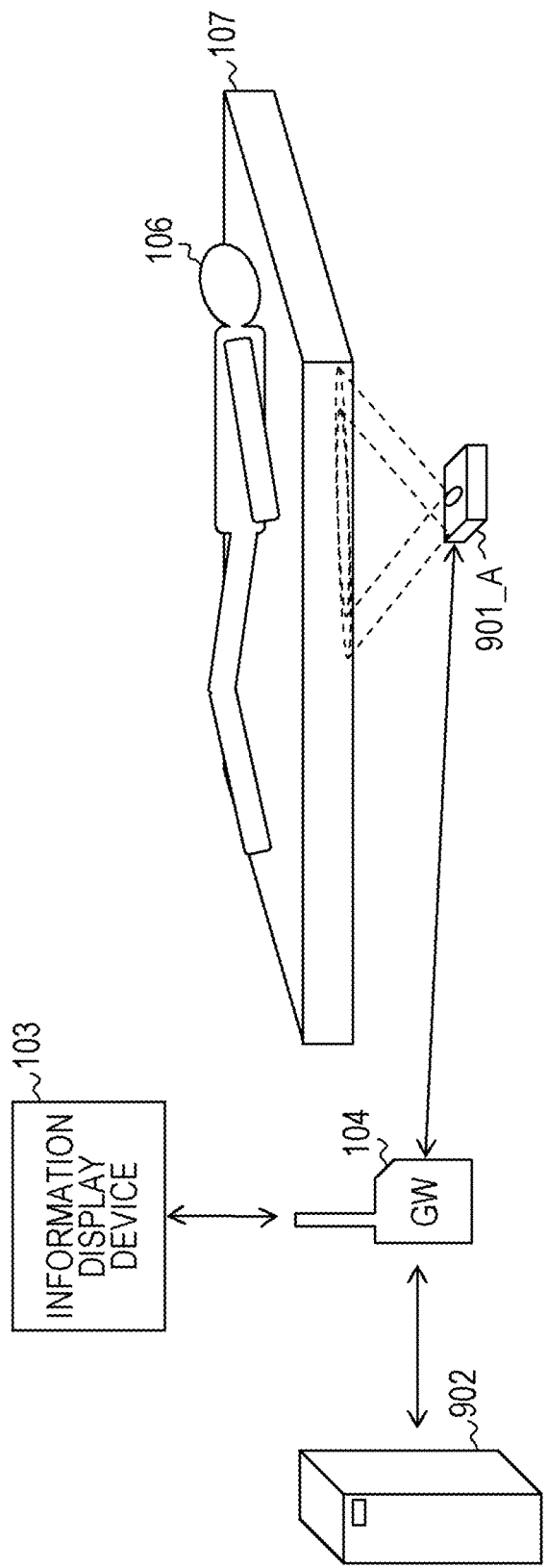
FIG. 23 is a diagram illustrating an overview of a biological information sensing device to which an information processing device according to a modified example 9 of the present disclosure is applied.

FIG. 23 is a diagram illustrating an overview of a biological information sensing device to which an information processing device according to a modified example 9 of the present disclosure is applied. The modified example 9 is an example in which the sensing device 901_A is placed under the bed 107 in the biological information sensing device according to Embodiment 2. Even in the case where the sensing device 901_A is placed under the bed 107, the activity amount data can be measured as in Embodiment 2.

Modified Example 10

In Embodiment 2, the body motion value, the heart rate, and the pulse rate are employed as the activity amount. Alternatively, at least one of those may be employed as the activity amount.

Modified Example 11

In Embodiment 1, it is described that the change detection section 307 generates the alerting information indicating abnormal body temperature of the human body 106. However, the present disclosure is not limited thereto. For example, the change detection section 307 may generate, as a comparison result, a difference between the body temperature of the human body 106 calculated from thermal image data and the reference value, and transmits information indicating the difference to the information display section 103A via the transmission section 308.

Modified Example 12

In Embodiment 2, it is described that the change detection section 907 generates the alerting information indicating abnormal activity amount of the human body 106. However, the present disclosure is not limited thereto. The change detection section 907 may generate, as a comparison result, a difference between the activity amount of the human body 106 calculated from activity amount data and the reference value, and transmits information indicating the difference to the information display section 103A via the transmission section 308. Since the activity amount data includes the body motion value, the breathing rate, and the heart rate, the change detection section 907 may include in the comparison result the differences from the reference values for respective ones of the body motion value, the breathing rate, and the heart rate.

The modified examples 1 to 8 may be applicable to both Embodiment 1 and Embodiment 2.

The information processing devices and the information processing methods according to respective embodiments of the present disclosure enable the obtainment of biological information in a non-invasive manner to human body, and further enable appropriate grasping of a biological state even if the position of a measurement target changes, thereby making them useful for daily recording of biological information and detection of a change in elder care and for controlling an air conditioner in conjunction with a body motion state.

What is claimed is:

1. An information processing method, comprising:
   obtaining measurement data for calculating biological information of a measurement subject from a sensor that performs measurement without contact;
   based on content of the measurement data,
      determining a direction of the measurement subject based on a contour of an extracted region of the measurement subject and a spatial relationship between a nose and a mouth in the extracted region of the measurement subject,
      classifying only a part of the measurement data corresponding to a whole face of the measurement subject into a group associated with at least the direction of the measurement subject,
      calculating the biological information from the classified part of the measurement data corresponding to the whole face of the measurement subject, and
   comparing the calculated biological information with a reference value associated with a group to which the part of the measurement data corresponding to the whole face of the measurement subject belongs; and
   making a notification based on a result of the comparing.

2. The information processing method according to claim 1,
   wherein in the classifying of the measurement data, the measurement data is classified into the group using a machine learning model, the machine learning model being a model having machine-learned about classification of the measurement data into the group based on content of the measurement data, and
   in the machine learning, the reference value is a representative value of the biological information in the group and is calculated from the measurement data classified into the group.

3. The information processing method according to claim 2, further comprising:
   causing the machine learning model to perform machine learning about classification of the measurement data into the group based on content of the measurement data,
   wherein in the machine learning, the representative value of the biological information in the group is calculated from measurement data classified into the group as the reference value of the group.

4. The information processing method according to claim 1,
   wherein the sensor is a thermal image sensor,
   the biological information is a body temperature,
   the measurement data is thermal image data obtained by the thermal image sensor,
   in the classifying the measurement data, the thermal image data is classified into the group based on a characteristic of a region indicating the measurement subject, the region being included in the thermal image data obtained by the thermal image sensor, and
   in the comparing, the body temperature of the measurement subject is calculated from classified thermal image data, and a calculated body temperature is compared with a reference value associated with a group to which the classified thermal image data belongs.

5. The information processing method according to claim 1,
   wherein the sensor is a radio wave sensor,
   the biological information is an activity amount including at least one of a body motion value, a breathing rate, and a heart rate of the measurement subject,
   the measurement data is activity amount data indicating the activity amount obtained by the radio wave sensor,
   in the classifying the measurement data, the activity amount data is classified into the group based on waveform information of the activity amount data obtained by the radio wave sensor, and
   in the comparing, the activity amount of the measurement subject is calculated from classified activity amount data, and a calculated activity amount is compared with a reference value associated with a group to which the classified activity amount data belongs.

6. An information processing method, comprising:
   obtaining measurement data for calculating biological information of a measurement subject from a sensor that performs measurement without contact;
   based on content of the measurement data, classifying the measurement data into a group associated with at least a position of the measurement subject, calculating the biological information from classified measurement data, and comparing calculated biological information with a reference value associated with a group to which the measurement data belongs;

making a notification based on a result of the comparing; and causing the machine learning model to perform machine learning about classification of the measurement data into the group based on content of the measurement data, wherein in the classifying of the measurement data, the measurement data is classified into the group using a machine learning model, the machine learning model being a model having machine-learned about classification of the measurement data into the group based on content of the measurement data, in the machine learning, the reference value is a representative value of the biological information in the group and is calculated from the measurement data classified into the group, in the machine learning, the representative value of the biological information in the group is calculated from measurement data classified into the group as the reference value of the group, and in a case where number of pieces of the measurement data not corresponding to any one of the groups exceeds a reference number, information prompting re-learning of the machine learning model is generated.

7. An information processing method, comprising:

obtaining measurement data for calculating biological information of a measurement subject from a sensor that performs measurement without contact;

obtaining time data indicating time of measurement of the measurement data;

based on content of the measurement data, classifying the measurement data into a group associated with at least a position of the measurement subject, calculating the biological information from classified measurement data, and comparing calculated biological information with a reference value associated with a group to which the measurement data belongs; and making a notification based on a result of the comparing, wherein in the comparing, whether or not the measurement data is measured at a predetermined time of day is determined based on the time data, and the comparing is performed when determined that the measurement data is measured at the predetermined time of day.

8. The information processing method according to claim 1, wherein the notification based on the comparing is a comparison result between the biological information and the reference value or abnormality of the measurement subject.

9. An apparatus, comprising:

a sensor that measures measurement data for calculating biological information of a measurement subject without contact;

a processor; and a memory storing thereon a computer program, which when executed by the processor, causes the processor to perform operations including:

obtaining the measurement data from the sensor;

based on content of the measurement data, determining a direction the measurement subject based on a contour of an extracted region of the measurement subject and a spatial relationship between a nose and a mouth in the extracted region of the measurement subject, classifying only a part of the measurement data corresponding to a whole face of the measurement subject into a group associated with at least the direction of the measurement subject;

calculating the biological information from the classified part of the measurement data corresponding to the whole face of the measurement subject, and comparing calculated biological information with a reference value associated with a group to which the part of the measurement data corresponding to the whole face of the measurement subject belongs; and making a notification based on a result of the comparing.

10. A non-transitory recording medium storing thereon a computer program, which when executed by the processor, causes the processor to perform operations according to claim 1.

* * * * *